(12) United States Patent
Yokota et al.

(10) Patent No.: US 9,056,105 B2
(45) Date of Patent: Jun. 16, 2015

(54) METHOD FOR TREATMENT OF BONE DISEASES AND FRACTURES

(75) Inventors: Hiroki Yokota, Carmel, IN (US); Ping Zhang, Indianapolis, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 792 days.

(21) Appl. No.: 13/055,399

(22) PCT Filed: Jul. 24, 2009

(86) PCT No.: PCT/US2009/051654
§ 371 (c)(1),
(2), (4) Date: Mar. 8, 2011

(87) PCT Pub. No.: WO2010/011898
PCT Pub. Date: Jan. 28, 2010

(65) Prior Publication Data
US 2011/0166180 A1 Jul. 7, 2011

Related U.S. Application Data

(60) Provisional application No. 61/083,752, filed on Jul. 25, 2008.

(51) Int. Cl.
*A61K 31/47* (2006.01)
(52) U.S. Cl.
CPC ...................................... *A61K 31/47* (2013.01)
(58) Field of Classification Search
CPC .................................................... A61K 31/147
USPC .......................................... 514/313, 580, 588
See application file for complete search history.

(56) References Cited

U.S. PATENT DOCUMENTS

2003/0099644 A1    5/2003   Ahuja et al.

OTHER PUBLICATIONS

Lindl, Kathryn A., "Activation of the Integrated Stress Response in HIV-Associated Neurocognitive Disorder" (2010). Publicly accessible Penn Dissertations. Paper 276.*
Lisse et al., PLOS Genetics, Feb. 2008, vol. 4, Issue 2, e7, p. 0001-0011.*
Shirakawa et al. (Molecular and Cellular Biology, Aug. 2006, p. 6105-6116).*
Nuttall et al (Current Opinion in Pharmacology 2004, 4:290-294).*
Hamamura et al. FEBS Letters 581 (2007) 1769-1774).*
International Search Report for PCT/US2009/051654 mailed on Sep. 4, 2009.
Zhang P, et al., Salubrinal stimulates anabolic responses in mouse femora, 55th Ann Meeting ORS (2009).
Zhang P, et al., Joint loading-driven bone formation and signaling pathways predicted from genome-wide expression profiles, Bone 44:989-998 (2009).
Bolland BJ, et al., "Development of in vivo μCT evaluation of neovascularisation in tissue engineered bone constructs," Bone 43:195-202 (2008).

(Continued)

*Primary Examiner* — Savitha Rao
*Assistant Examiner* — Angela Brown-Pettigrew

(57) ABSTRACT

Described herein are compounds, compositions, and methods useful for treating bone diseases or defects. Also described herein are compounds, compositions and methods for treating bone diseases or defects by inhibiting phosphatase complexes.

3 Claims, 25 Drawing Sheets

(56) References Cited

OTHER PUBLICATIONS

Zhu, Y., et al., "eIF-2α protects brainstem motoneurons in a murine model of sleep apnea," J. Neurosci. 28: 2168-2178 (2008).
Hamamura, K., et al., "Microarray analysis of thapsigargin-induced stress to the endoplasmic reticulum of mouse osteoblasts," *J. Bone Miner. Metab.* 26:231-240 (2008).
Eizirik, D.L., et al., "The role for endoplasmic reticulum stress in diabetes mellitus," Endocrine Reviews 29:42-61 (2008).
Baron, R., et al., "Minireview: targeting the Wnt/β-catenin pathway to regulate bone formation in the adult skeleton," *Endocrinol.* 148:2635-2643 (2007).
Zhang P., et al., Knee loading accelerates bone healing in mice, *J. Bone Miner. Res.* 22:1979-1987 (2007).
Cnop, M., et al., "Selective inhibition of eukaryotic translation initiation factor 2 alpha dephosphorylation potentiates fatty acid-induced endoplasmic reticulum stress and causes pancreatic beta-cell dysfunction and apoptosis," J. Biol. Chem. 282: 3989-3997 (2007).
Draghici, S., et al., "A systems biology approach for pathway level analysis," *Genome Res.* 17:1537-45 (2007).
Ron, D., et al., "eIF2α phosphorylation in cellular stress responses and disease," Translational Cont. Biol. Med. 13:349-372 (2007).
Hamamura, K., et al., "Stress to endoplasmic reticulum of mouse osteoblasts induces apoptosis and transcriptional activation for bone remodeling," FEBS Lett. 381:1769-1774 (2007).
Sokka, A.L., et al., "Endoplasmic reticulum stress inhibition protects against excitotoxic neuronal injury in the rat brain," J. Neurosci. 27: 901-908 (2007).
Wang JW, et al., "Locally applied simvastatin promotes fracture healing in ovariectomized rat," *Osteoporosis Int.* 18:1641-1650 (2007).
Costa-Mattioli, M., et al., "eIF2alpha phosphorylation bidirectionally regulates the switch from short- to long-term synaptic plasticity and memory," Cell 129:195-206 (2007).
Wek, R., et al., "Translational control and the unfolded protein response," Antioxidants and Redox Signaling 9:1-15 (2007).
Worsham DN, et al., In vivo gene transfer into adult stem cells in unconditioned mice by in situ delivery of a lentiviral vector, Mol. Ther. 14:514-24 (2006).
Barragan-Adjemian, C., et al., "Mechanism by which MLO-A5 late osteoblasts/early osteocytes mineralize in culture: similarities with mineralization of lamellar bone," *Calcif. Tissue Int.* 79:340-353 (2006).
Szegezdi, E., et al., "Mediators of endoplasmic reticulum stress-induced apoptosis," EMBO Rep. 7: 880-885 (2006).
Zhang, P., et al., "Knee loading causes diaphyseal cortical bone formation in murine femurs," *BMC Musculoskelet Dis.* 73:1-12 (2006).
Yokota, H., et al., "Osteogenic potentials with joint loading modality," *J. Bone Miner. Metab.* 23:302-308 (2005); Zhang, P., et al., "Bone formation in mouse tibia with knee-loading modality," *J. Appl. Physiol.* 100:1452-1459 (2006).
Boyce, M., et al., "Cellular response to endoplasmic reticulum stress: a matter of life or death," Cell Death Differ. 13:363-373 (2006).
Gilchrist, M., et al., "Systems biology approaches identify ATF3 as a negative regulator of Toll-like receptor 4," *Nature* 441:173-178 (2006).
Marciniak, S.J., et al., "CHOP induces death by promoting protein synthesis and oxidation in the stressed endoplasmic reticulum," *Genes & Develop.* 18:3066-3077 (2006).

Zhao, L., et al., "Endoplasmic reticulum stress in health and disease," Current Opinion Cell Biol. 18:444-452 (2006).
Long, K., et al., "Structure-Activity relationship studies of salubrinal lead to its active biotinylated derivative," *Bioorganic & Medicinal Chemistry Letters*, 15:3849-3852 (2005).
Costa-Mattioli, M., et al., "Translational control of hippocampal synaptic plasticity and memory by the eIF2alpha kinase GCN2," Nature 436:1166-1173 (2005).
Janssens, K., et al., "Transforming growth factor-beta1 to the bone," *Endocr. Rev.* 26:743-774 (2005).
Boyce, M., et al., "A selective inhibitor of eIF2α dephosphorylation protects cells from ER stress," Science 307: 935-939(2005).
Proud, C.G., "eIF2 and the control of cell physiology," Semin. Cell Dev. Biol. 16: 3-12 (2005).
Yang, X., et al., "ATF4 is a substrate of RSK2 and an essential regulator of osteoblasts biology: implication for Coffin-Lowry syndrome," Cell 117:387-398 (2004).
Vattem, K.M., et al., "Reinitiation involving upstream ORFs regulates ATF4 mRNA translation in mammalian cells," Proc. Natl. Acad. Sci. U.S.A. 101:11269-11274 (2004).
Whiteman, P., et al., "Defective secretion of recombinant fragments of fibrillin-1: implications of protein misfolding for the pathogenesis of Marfan syndrome and related disorders," Hum. Molec. Genet. 7:727-737 (2003).
Harding, H.P., et al., "An integrated stress response regulates amino acid metabolism and resistance to oxidative stress," Mol. Cell 11: 619-633 (2003).
Kaneko M, et al., "Human HRD1 protects against ER stress-induced apoptosis through ER-associated degradation," FEBS Lett. 532:147-52 (2003).
Harding, H.P., et al., "Transcriptional and translational control in the mammalian unfolded protein response," Annu. Rev. Dev. Biol. 18:575-599 (2002).
Ron, D., "Translational control in the endoplasmic reticulum stress response," J. Clin. Inv. 110:1383-1388 (2002).
Kim HK, et al., "Histopathologic Changes in Growth-Plate Cartilage Following Ischemic Necrosis of the Capital Femoral Epiphysis : An Experimental Investigation in Immature Pigs," J Bone Joint Surg Am 83:688-697 (2001).
Tamura, Y., et al., "Focal adhesion kinase activity is required for bone morphogenetic protein—Smad1 signaling and osteoblastic differentiation in murine MC3T3-E1 cells," *J. Bone Miner Res.* 16:1772-1779 (2001).
Chiba S., et al., "Molecular analysis of defect healing in rat diaphyseal bone," *J. Vet. Med. Sci.* 63:603-606 (2001).
Ye, Y., et al., "The AAA ATPase Cdc48/p97 and its partners transport proteins from the ER into the cytosol," Nature 414:652-656 (2001).
Xiao, G., et al., "Ascorbic acid-dependent activation of the osteocalcin promoter in MC3T3-E1 preosteoblasts: requirement for collagen matrix synthesis and presence of an intact OSE2 sequence," *Mol. Endocrinol.* 11:1103-1113 (1997).
Sponseller, P.D., et al., "The thoracolumbar spine in Marfan syndrome," J. Bone Joint Surg. 77-A:867-876 (1995).
Rixon, R.H., et al., "Parathyroid fragments may stimulate bone growth in ovariectomised rats by activating adenylyl cyclase," J. Bone Min Res, 9:1179-1189 (1994).
M. Gunness-Hey & J. M. Hock, "Increased Trabecular Bone Mass in Rats Treated with Human Synthetic Parathyroid Hormone," Metab. Bone Dis. Rel. Res., 5:177-181 (1984).

\* cited by examiner

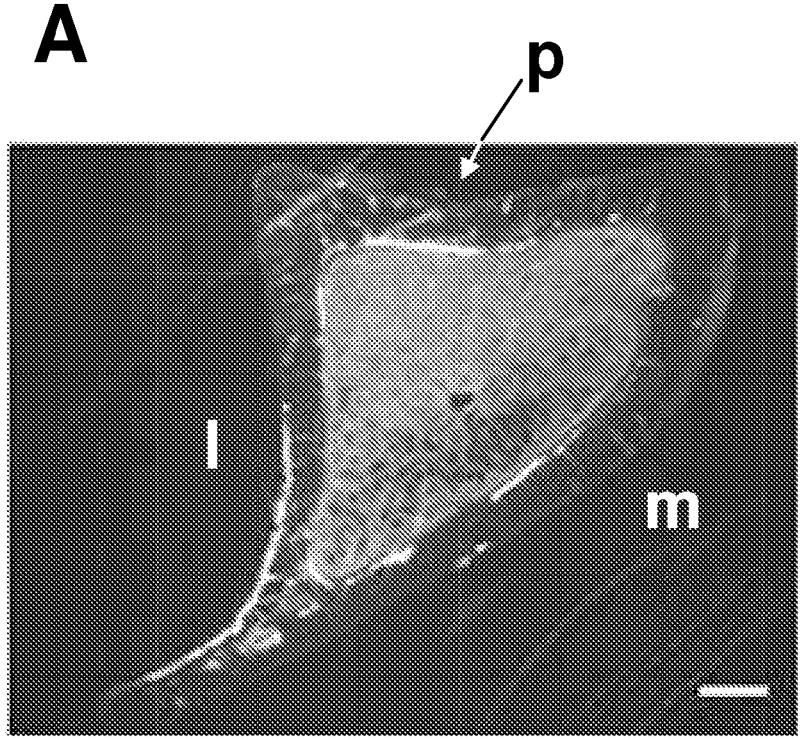
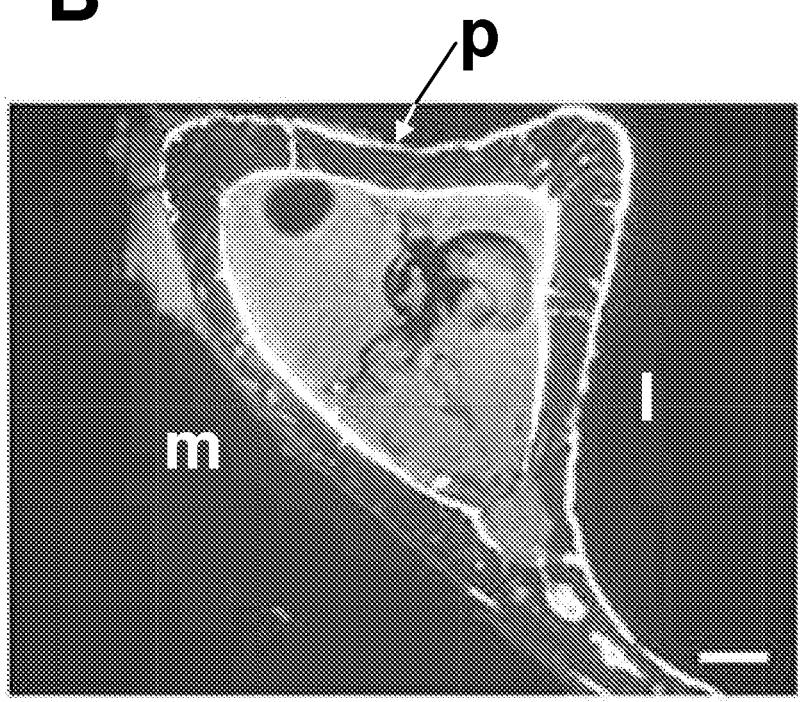
Fig. 3

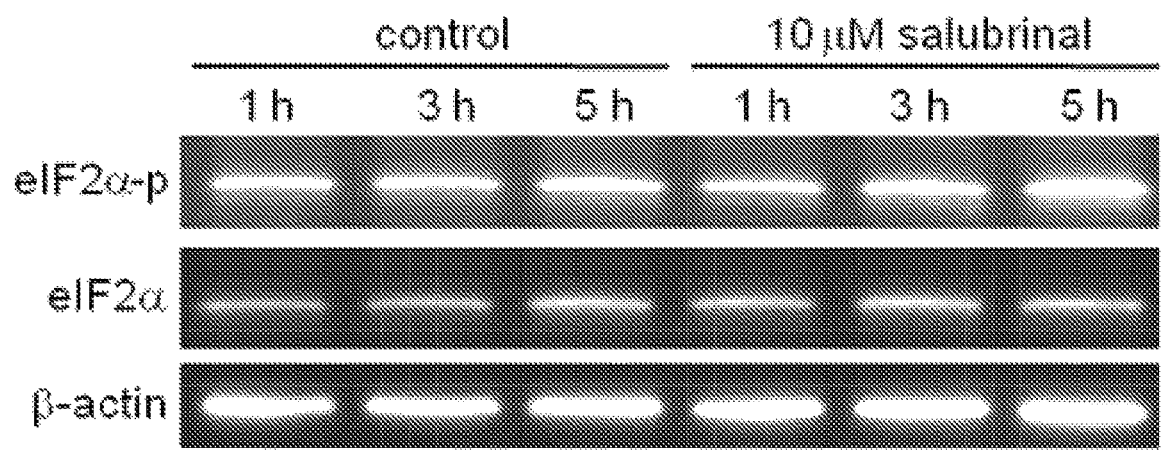
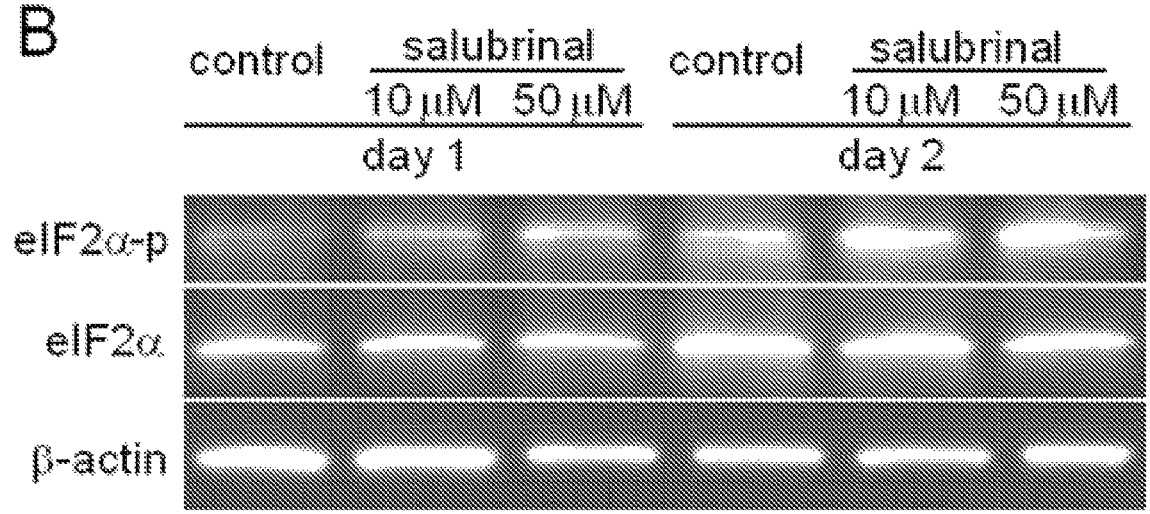
Fig. 13

(V)            (T)
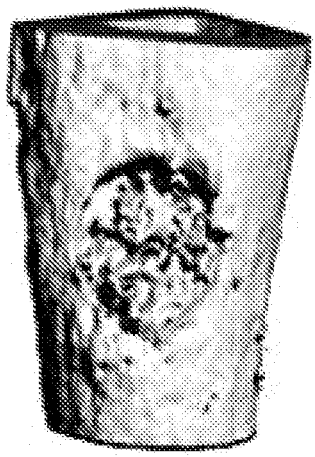 
 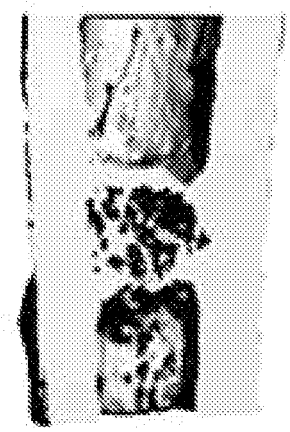
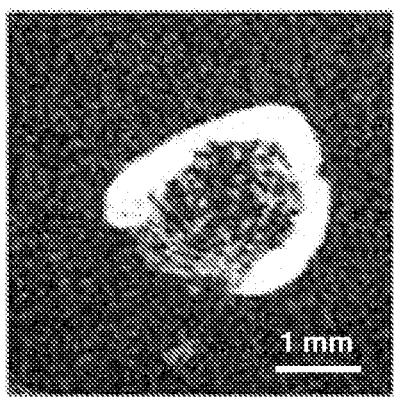 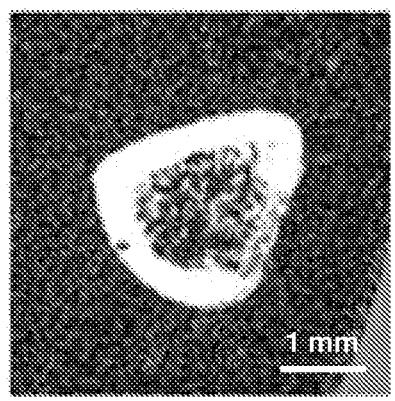
Fig. 16A (V) 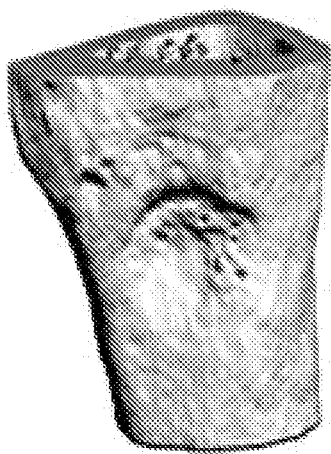 (T) 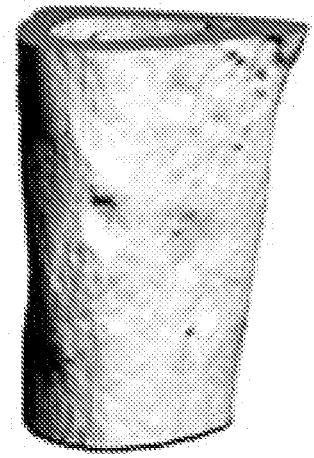
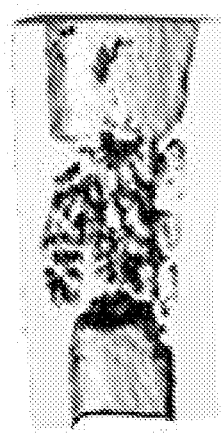 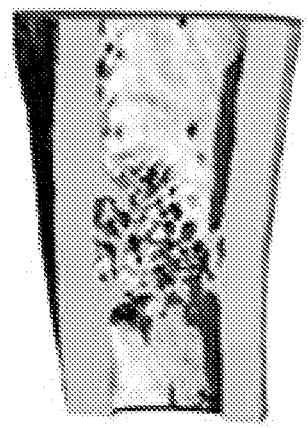
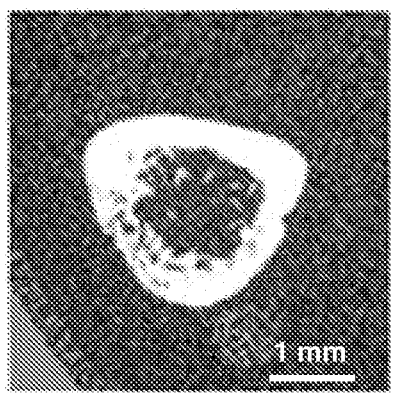 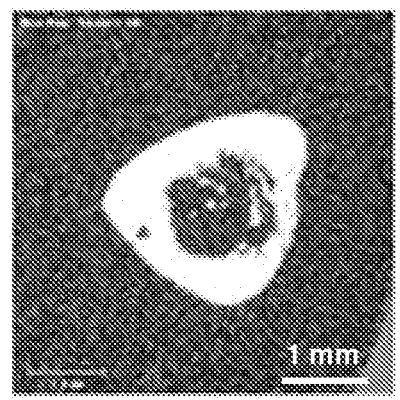
Fig. 16B

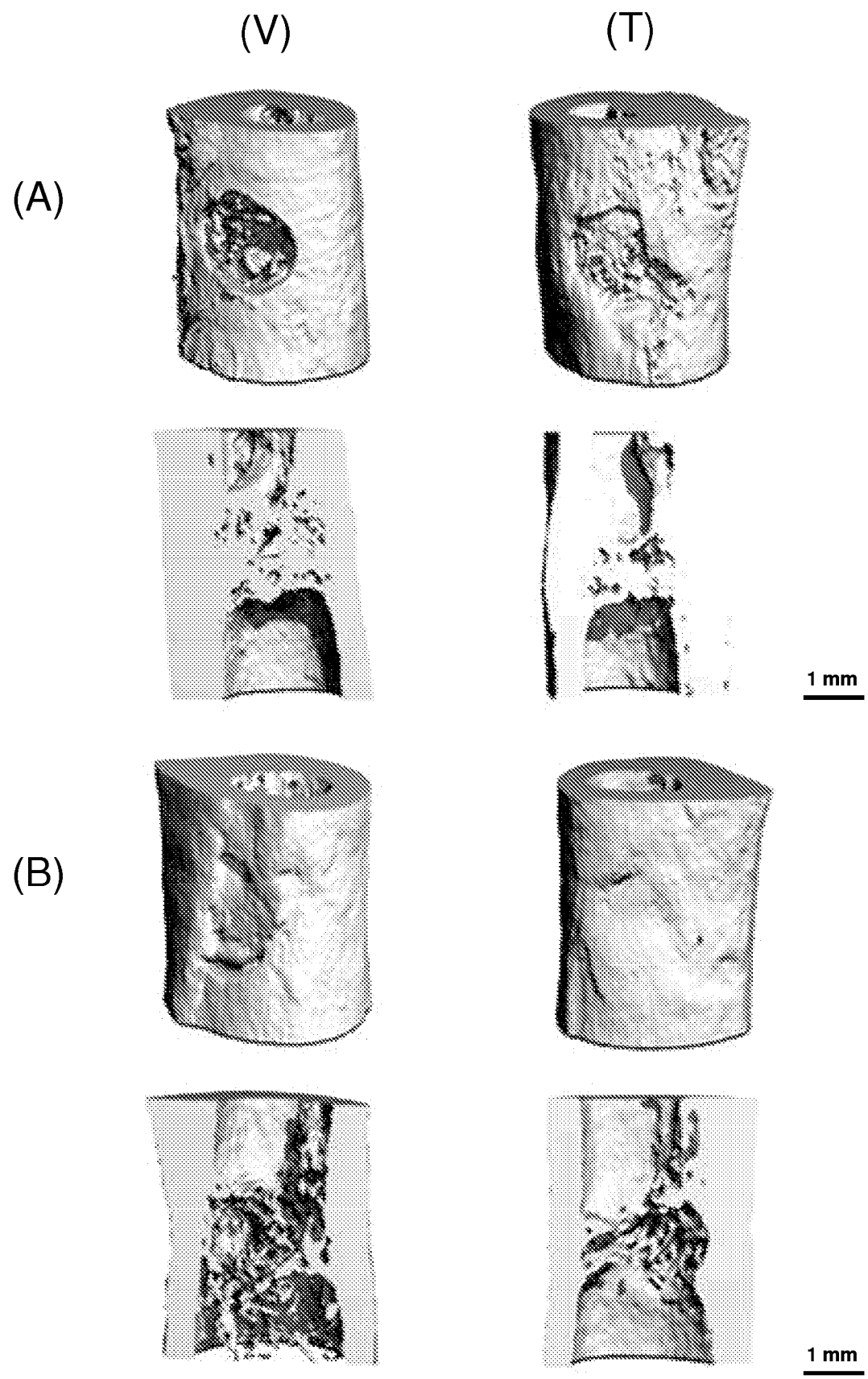
Fig. 19A & B

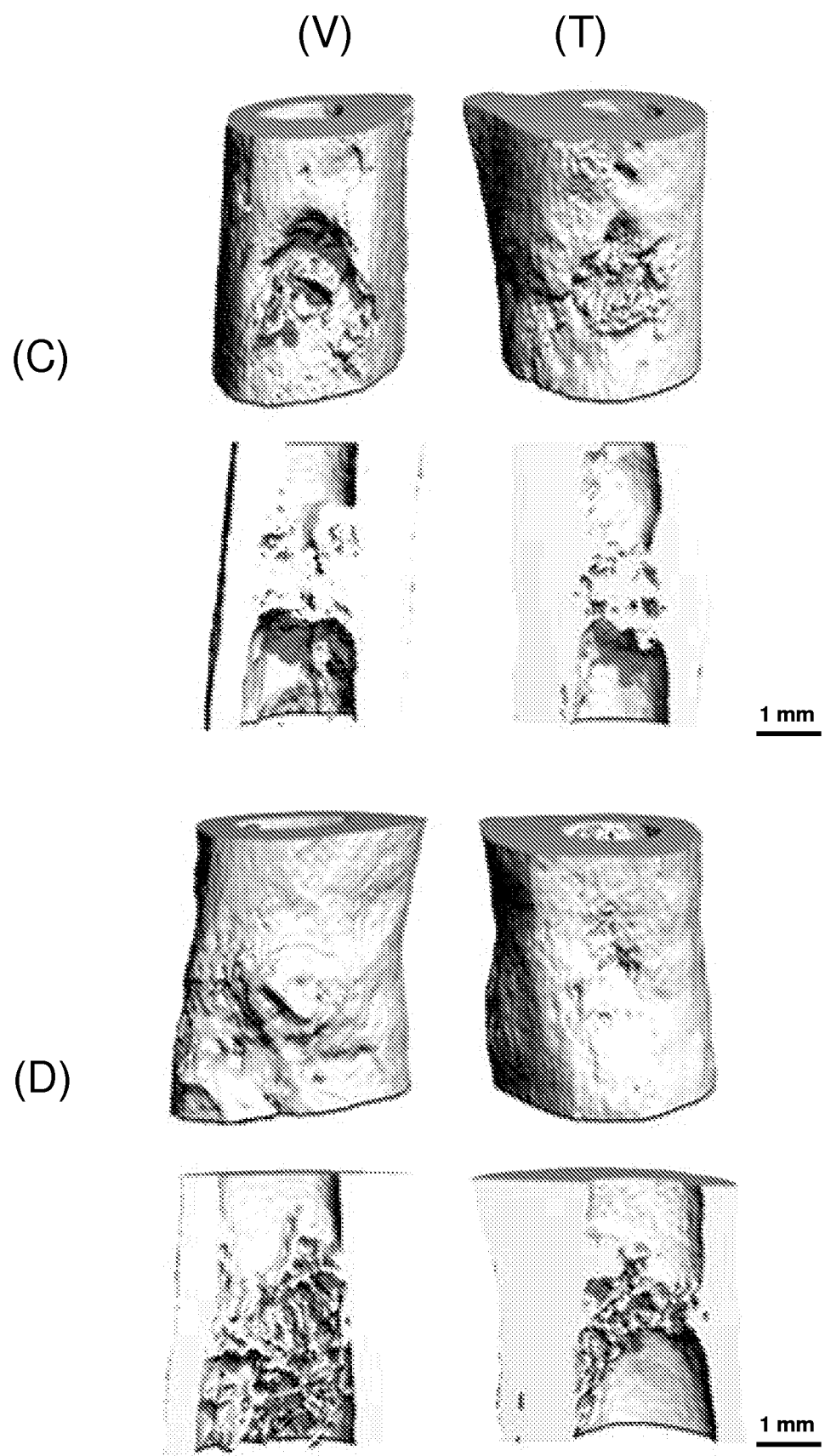
Fig. 19 C & D

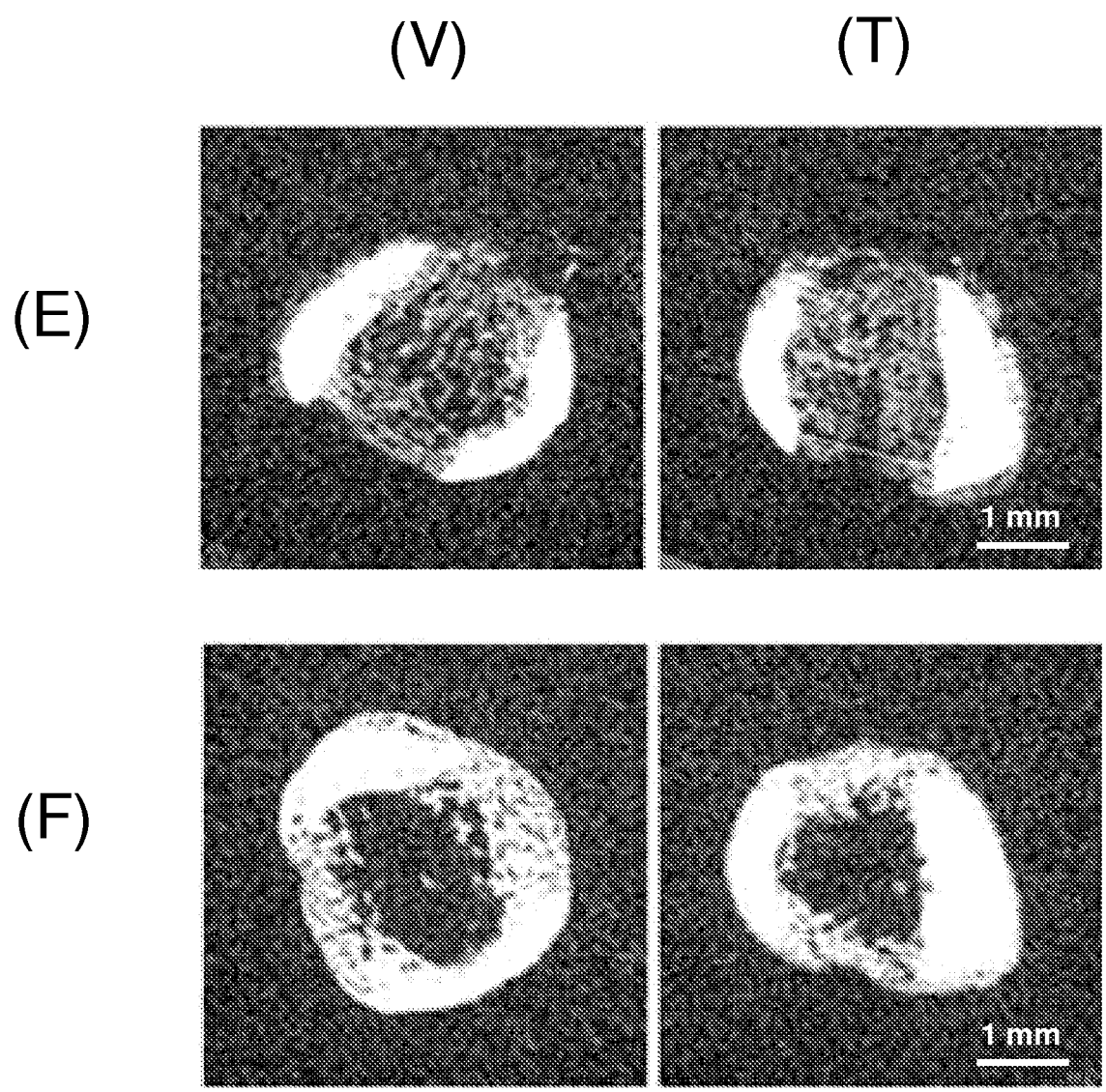
Fig. 19 E & F (A)
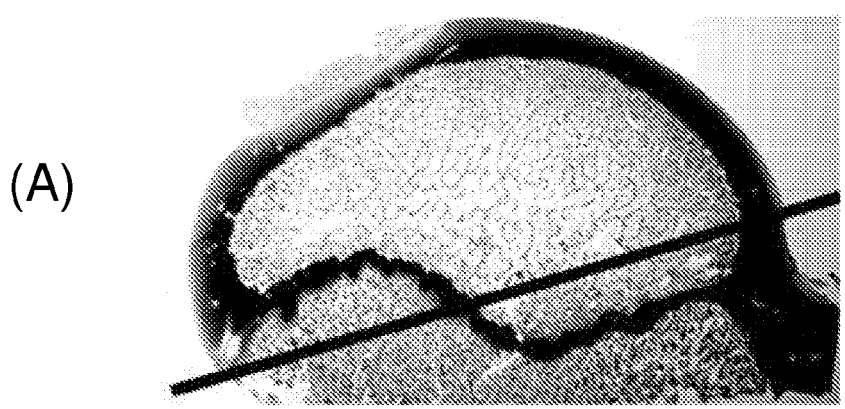
(B)
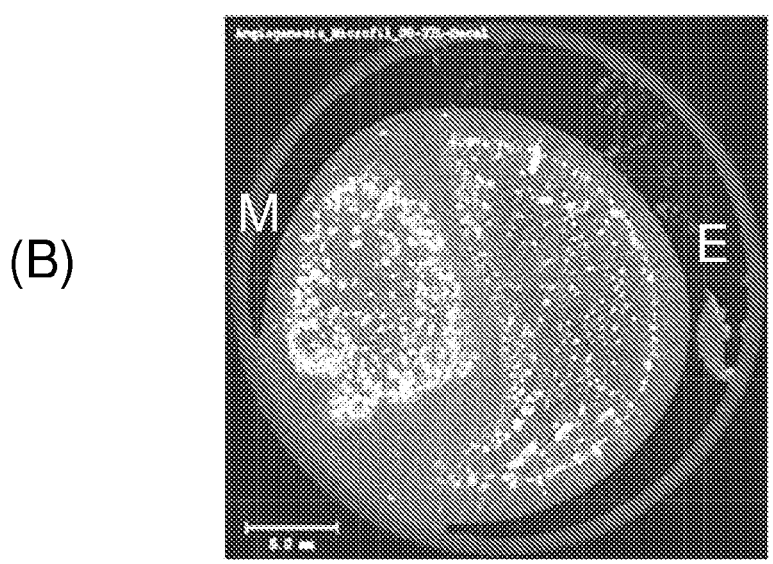
(C)
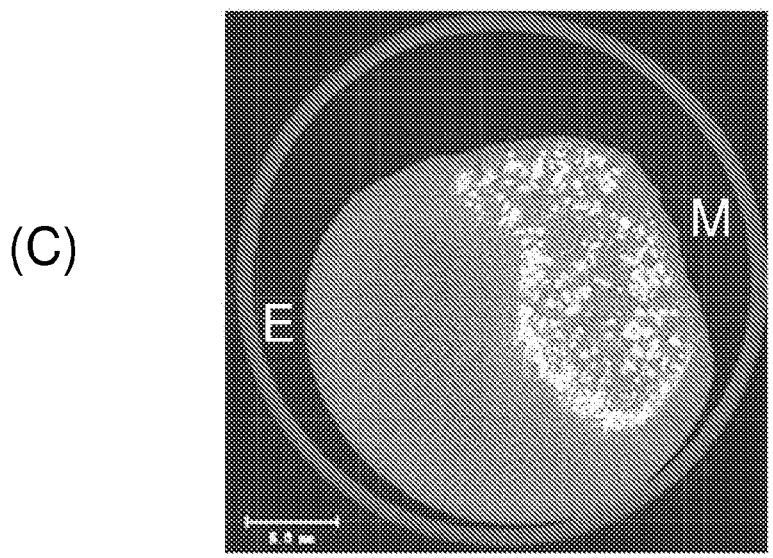
Fig. 22

METHOD FOR TREATMENT OF BONE DISEASES AND FRACTURES

CROSS-REFERENCE TO RELATED APPLICATIONS

This application is a U.S. national application under 35 U.S.C. §371(b) of International Application Serial No. PCT/US2009/051654 filed Jul. 24, 2009, which claims the benefit under 35 U.S.C. §119(e) of priority U.S. provisional patent application Ser. No. 61/083,752, filed Jul. 25, 2008, the disclosures of both of which are incorporated herein by reference in their entirety.

GOVERNMENT RIGHTS

This invention was made with government support under R01 AR052144 awarded by The National Institutes of Health. The U.S. Government has certain rights in the invention.

TECHNICAL FIELD

The invention described herein pertains to compositions and methods for treating diseases or disorders arising from apoptosis. In particular, the invention described herein pertains to compositions and methods for treating diseases or disorders arising from integrated stress response-induced apoptosis, such as occurs in bone diseases, injuries, and defects.

BACKGROUND AND SUMMARY OF THE INVENTION

Diverse environmental stresses including hypoxia, oxidative stress, viral infection, nutrient limitation, radiation, ischemia, and others. Such stresses may affect a variety of tissues, including membranes, cytoplasm, the endoplasmic reticulum (ER), and the like. Stress to the ER has been reported to harm the efficient functioning of protein folding and cellular activities (Harding, H. P., et al., "Transcriptional and translational control in the mammalian unfolded protein response," Annu. Rev. Dev. Biol. 18:575-599 (2002); Szegezdi, E., et al., "Mediators of endoplasmic reticulum stress-induced apoptosis," EMBO Rep. 7: 880-885 (2006); Wek, R., et al., "Translational control and the unfolded protein response," Antioxidants and Redox Signaling 9:1-15 (2007)). In order to alleviate cellular injury or, conversely, initiate apoptotic cell death, cells induce the ISR (Harding, H. P., et al., "An integrated stress response regulates amino acid metabolism and resistance to oxidative stress," Mol. Cell. 11: 619-633 (2003)). The ISR evokes translational reprogramming as its primary consequence and secondarily affects the transcriptional profile of cells. ER stress is one type of ISR induced stress (Ron, D., "Translational control in the endoplasmic reticulum stress response," J. Clin. Inv. 110:1383-1388 (2002); Boyce, M., et al., "Cellular response to endoplasmic reticulum stress: a matter of life or death," Cell Death Differ. 13:363-373 (2006)). The foregoing publications and all other additional publications cited herein are incorporated herein by reference.

Stress to the ER has been implicated in type 2 (non-insulin dependent) diabetes, Wolfram Syndrome, tyrosinemia, cystic fibrosis, tumor growth under hypoxic conditions, cerebral ischemia, neurodegenerative diseases (Familial Amyotrophic Lateral Aclerosis, Familial Alzheimer's disease, Hunting-ton's disease), and others. However, whether this stress to the ER is a primary cause of diseases or only a secondary pathological phenomenon is currently being debated (Zhao, L., et al., "Endoplasmic reticulum stress in health and disease," Current Opinion Cell Biol. 18:444-452 (2006)). In skeletal diseases that are linked to stress to the ER, four specific genetic disorders are listed in "Online Mendelian Inheritance in Man (OMIM)" database.

One such genetic disorder, Wolcott-Rallison Syndrome, is an autosomal recessive disorder characterized by epiphyseal dysplasia, osteoporosis and permanent neonatal or early infancy insulin-dependent diabetes. In two unrelated patients with Wolcott-Rallison syndrome, two mutations in the EIF2AK3 gene (PERK) were identified. Another disorder, Synovial cell hyperplasia, results in destruction caused by mutations in SYVN1 (synovial apoptosis inhibitor 1; HRD1). SYVN1 is a ubiquitin ligase whose expression is induced by the unfolded protein response following stress to the ER (Kaneko M, et al., "Human HRD1 protects against ER stress-induced apoptosis through ER-associated degradation," FEBS Lett. 532:147-52 (2003)). Expression of HRD1 protects cells from apoptosis by inducing degradation of abnormally processed proteins that accumulate in the ER. Another disorder, Inclusion Body Myopathy with Paget Disease of Bone and Frontotemporal Dementia (IBMPFD), is characterized by adult-onset proximal and distal muscle weakness (clinically resembling a limb-girdle muscular dystrophy syndrome), early-onset Paget Disease of Bone, and premature frontotemporal dementia (FTD). IBMPDF is caused by mutation in VCP (valosin-containing protein), which is required for the export of ER proteins into the cytosol (Ye, Y., et al., "The AAA ATPase Cdc48/p97 and its partners transport proteins from the ER into the cytosol," Nature 414:652-656 (2001)). Cardiac failure and cardiomyopathy have been observed in later stages. Paget Disease of Bone involves focal areas of increased bone turnover that typically lead to spine and/or hip pain and localized enlargement and deformity of the long bones. Another disorder, Marfan Syndrome, is characterized by disproportionately long limbs and digits, anterior chest deformity, mild to moderate joint laxity, and vertebral column deformity (scoliosis and thoracic lordosis) (Sponseller, P. D., et al., "The thoracolumbar spine in Marfan syndrome," J. Bone Joint Surg. 77-A:867-876 (1995)). This syndrome is caused by missense mutations in FBN1 (fibrillin-1), which increases retention of mutated products in the ER (Whiteman, P., et al., "Defective secretion of recombinant fragments of fibrillin-1: implications of protein misfolding for the pathogenesis of Marfan syndrome and related disorders," Hum. Molec. Genet. 7:727-737 (2003)).

Without being bound by theory, it is believed herein that genetic diseases, such as Wolcott-Rallison syndrome, synovial cell hyperplasia, IBMPFD (Inclusion Body Myopathy associated with Paget disease of bone and Frontotemporal Dementia), and Marfan syndrome are directly or indirectly linked to the biological process of coping with stress to the ER, a form of integrated stress response (ISR) where translational regulation plays a key role. IBMPFD and Marfan syndrome are linked to stress to the ER, and in particular are linked to abnormal retention of mutated proteins in the ER. In Wolcott-Rallison syndrome the responses to the ER stress are impaired by the kinase for phosphorylation of eIF2α, while in mutation in SYVN1 bone destruction is triggered by insufficient protection of cells from ER stress-induced apoptosis. In addition, but without being bound by theory, it is believed herein that many skeletal diseases, including bone disorders, diseases, and even complications arising from bone injury are directly or indirectly linked to the biological process of coping with stress to the ER. One such bone disease is osteoporosis, which is most common in women after menopause but may also develop in elderly men. Osteoporosis is a bone disease that reduces bone mass and strength. Because of its risk of fracture in the femoral neck and long bones, it significantly affects quality of life.

Although the role of stress to the ER may differs in those diseases, though without being bound by theory, it is believed herein that active intervention in regulating stress to the ER and other ISR with pharmacological agents, with or without mechanical stimulation, will elevate anabolic responses in vitro and in vivo.

Phosphorylation of the alpha subunit of eukaryotic translation initiation factor 2 (eIF2α) is a highly conserved regulatory event activated during ISR (Ron, D., et al., "eIF2α phosphorylation in cellular stress responses and disease," Translational Cont. Biol. Med. 13:349-372 (2007)). ISR-driven phosphorylation on serine 51 of eIF2α blocks an exchange process of eukaryotic translation initiation factor 2B (eIF2B) from GDP-bound eIF2 to GTP-bound eIF2 (Proud, C. G., "eIF2 and the control of cell physiology," Semin. Cell Dev. Biol. 16: 3-12 (2005)). Consequently, the global translation-initiation is suppressed except for a group of specific genes whose expression is crucial for an adaptive response for survival.

One such gene translationally activated in ISR is the transcriptional regulator activating transcription factor, ATF4. ATF4 mRNA consists of two upstream open reading frames (uORF) (uORF1 and uORF2) together with the ATF4-coding region (Vattem, K. M., et al., "Reinitiation involving upstream ORFs regulates ATF4 mRNA translation in mammalian cells," Proc. Natl. Acad. Sci. U.S.A. 101:11269-11274 (2004)). When eIF2-GTP is abundant in non-stressed cells, ribosomes scanning downstream of uORF1 reinitiate translation at uORF2 that aborts translation of ATF4 protein. During the ISR process, reduction in the levels of eIF2-GTP promotes non-commitment of ribosomes at uORF2 and increases re-initiation of translation at the ATF4-coding region.

ATF4 is also an essential regulator in bone development and its deficiency in transgenic mice results in a phenotype having delayed bone formation as well as low bone mass (Yang, X., et al., "ATF4 is a substrate of RSK2 and an essential regulator of osteoblasts biology: implication for Coffin-Lowry syndrome," Cell 117:387-398 (2004)). In addition to ATF4, it is believed herein that other ISR-linked genes may be important in bone development, including ATF3 and CHOP. Further, genes that are involved in bone remodeling, including Runx2, Osterix, and Rank 1, may be also affected by active intervention in regulating stress to the ER and other ISR.

A number of pharmacological agents are known to promote phosphorylation of eIF2α, including thapsigargin (Wek, R., et al., "Translational control and the unfolded protein response," Antioxidants and Redox Signaling 9:1-15 (2007)) and tunicamycin. MC3T3 mouse osteoblast-like cells have been incubated with thapsigargin ($C_{34}H_{50}O_{12}$; M.W. 651) and tunicamycin ($C_{39}H_{64}N_4O_{16}$; M.W. 840) (Hamamura, K., et al., "Stress to endoplasmic reticulum of mouse osteoblasts induces apoptosis and transcriptional activation for bone remodeling," FEBS Lett. 381:1769-1774 (2007)). Although both agents activate PERK, their mechanisms are different. Thapsigargin raises a cytosolic calcium concentration by blocking $Ca^{++}$ pumps, while tunicamycin is an inhibitor of N-linked glycosylation and the formation of N-glycosidic protein-carbohydrate linkages.

It is suggested herein that there are two ways for pharmacological agents to regulate phosphorylation of eIF2α, as inhibitors of dephosphorylation and as inducers of phosphorylation. Described herein are compounds, compositions, and methods useful for inhibition of dephosphorylation. Salubrinals are one such family of compounds capable of acting as inhibitors of dephosphorylation. The parent compound salubrinal ($C_{21}H_{20}Cl_3N_4OS$; M.W. 479.8) has been reported to protect the rat pheochromocytoma cell line from ER stress-induced apoptosis (Boyce, M., et al., "A selective inhibitor of eIF2α dephosphorylation protects cells from ER stress," Science 307: 935-939 (2005)). In addition, the effect of salubrinal was examined using a rat neuronal injury model in which acute ER stress was induced by the glutamate receptor agonist kainic acid. The results revealed that intra-cerebroventricular or intra-peritoneal administration decreased excitotoxic neuronal death in vivo (Sokka, A. L., et al., "Endoplasmic reticulum stress inhibition protects against excitotoxic neuronal injury in the rat brain," J. Neurosci. 27: 901-908 (2007)). Furthermore, administration of salubrinal to brainstem motoneurons in mice suppressed motoneuronal injury in response to hypoxia and reoxygenation events (Zhu, Y., et al., "eIF-2α protects brainstem motoneurons in a murine model of sleep apnea," J. Neurosci. 28: 2168-2178 (2008)). Direct injection into a mouse hippocampus modulated ATF4-dependent long-term synaptic plasticity and memory (Costa-Mattioli, M., et al., "Translational control of hippocampal synaptic plasticity and memory by the eIF2alpha kinase GCN2," Nature 436: 1166-1173 (2005); Costa-Mattioli, M., et al., "eIF2alpha phosphorylation bidirectionally regulates the switch from short- to long-term synaptic plasticity and memory," Cell 129:195-206 (2007)).

In contrast, the potential benefits of salubrinal to β-cells is reportedly controversial. While β-cell loss in type 1 diabetes is an autoimmune-mediated process and a linkage to ER stress is yet to be examined, type 2 diabetes results from a reduced ability of β-cells to secrete enough insulin to stimulate glucose utilization. Thus, accumulating evidence indicates that stress to the ER plays a role in β-cell dysfunction and death in type 2 diabetes (Eizirik, D. L., et al., "The role for endoplasmic reticulum stress in diabetes mellitus," Endocrine Reviews 29:42-61 (2008)). However, administration of 5-75 μM salubrinal induced apoptosis in rat β-cells in a dosage dependent manner, demonstrating that excessive eIF2α phosphorylation is poorly tolerated by β-cells (Cnop, M., et al., "Selective inhibition of eukaryotic translation initiation factor 2 alpha dephosphorylation potentiates fatty acid-induced endoplasmic reticulum stress and causes pancreatic beta-cell dysfunction and apoptosis," J. Biol. Chem. 282: 3989-3997 (2007)). Thus, without being bound by theory, it is believed herein that the effects of salubrinal are dependent both on dosage and cell type. Further, it is believed herein that in β-cells it is possible that phosphorylation of eIF2α plays a dual role, acting as beneficial regulator of insulin production or as trigger of dysfunction and apoptosis. Alternatively, salubrinal may have toxic side effects unlinked to eIF2α phosphorylation in β-cells and other specific cells. Also, but without being bound by theory, it is believed herein that strong and/or prolonged exposure to stress also leads to apoptosis.

Though the consequences of promoting and/or maintaining phosphorylation of eIF2α are still being investigated, it has been discovered herein that inhibition of one or more phosphatase complexes by salubrinal, and derivatives thereof, thus promoting and/or maintaining phosphorylation of eIF2α, may represent a viable method for treating integrated stress response-induced apoptosis, including ER stress-induced apoptosis. Accordingly, bone diseases, such as osteoporosis, bone defects, bone injuries, such as fractures, and other bone conditions, arising from or exacerbated by such induced apoptosis may be treated using the compounds, compositions, and methods described herein.

In one illustrative embodiment of the invention, compounds, pharmaceutical compositions thereof, and methods for using each are described herein for inhibiting phosphatase complexes in treating diseases that arise from apoptosis of certain cell populations. In one aspect, the compounds, pharmaceutical, and methods are described for treating integrated stress response-induced apoptosis. It is appreciated herein that a wide variety of diseases in a wide variety of tissues may be caused by integrated stress response-induced apoptosis. In another embodiment, compounds, compositions, and methods are described herein for treating diseases that arise from endoplasmic reticulum stress-induced apoptosis. In another embodiment, compounds, compositions, and methods are described herein for inhibiting the dephosphorylation of, maintaining the phosphorylation of, and/or promoting the phosphorylation of eIF2α.

In another illustrative embodiment, compounds, compositions, and methods are described herein for inhibiting one or more phosphatase complexes, wherein the inhibition prevents eIF2α dephosphorylation at the endoplasmic reticulum of the cell below a threshold where apoptosis might otherwise occur. In one variation, the inhibition results in or also results in maintaining the eIF2α phosphorylation at the endoplasmic reticulum of the cell above a threshold level where apoptosis might otherwise occur. In another variation, the inhibition results in or also results in stabilizing the eIF2α phosphorylation state of the endoplasmic reticulum of the cell above a threshold level where apoptosis might otherwise occur.

In another embodiment, compounds, compositions, and methods are described herein for treating a bone disease, bone, bone injury, and/or bone defect. Illustrative diseases, disorder, injuries, defects, and the like include, but are not limited to, osteoporosis, osteopenia, fracture, surgical wounds, spinal bone defects, osteonecrosis, pediatric hip necrosis, osteonecrosis of the jaw bone, bone defects or degradation arising from cancer treatment, including chemotherapy, radiation therapy, and the like.

In another embodiment, the compounds, compositions, and methods described herein include one or more salubrinals, including salubrinal, and analogs and derivatives of salubrinal, and/or pharmaceutically acceptable salts thereof, hydrates thereof, and/or solvates thereof, and/or a prodrug of any of the foregoing. It is to be understood, that as used herein, the term "salubrinal" may refer both to the individual compound as well as the family of compounds that include such analogs and derivatives. In another embodiment, the salubrinals are of the formula

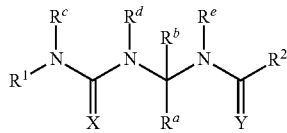

or a pharmaceutically acceptable salt thereof, wherein:

X and Y are independently O or S;

$R^1$ is alkyl, cycloalkyl, alkenyl, cycloalkenyl, aryl, or heteroaryl, each of which is optionally substituted;

$R^2$ is alkyl, cycloalkyl, alkenyl, cycloalkenyl, aryl, heteroaryl, cycloalkylalkyl, cycloalkenylalkyl, arylalkyl, heteroarylalkyl, cycloalkylalkenyl, cycloalkenylalkenyl, arylalkenyl, or heteroarylalkenyl, each of which is optionally substituted;

$R^a$ is optionally substituted alkyl;

$R^b$ is H or optionally substituted $C_1$-$C_6$ alkyl;

$R^c$, $R^d$, and $R^e$ are each independently selected from the group consisting of H, optionally substituted $C_1$-$C_6$ alkyl, acyl, or a prodrug capable of releasing the attached nitrogen in vivo to form the corresponding H or salt derivative thereof;

and A and B are independently H, or optionally substituted $C_1$-$C_6$ alkyl.

In another embodiment, a therapeutically effective amount of a compound described herein, such as salubrinal, or an analog or derivative thereof, is administered to a patient in need of relief from a bone disease, injury, or defect. In another embodiment, a therapeutically effective amount of a compound described herein, such as salubrinal, or an analog or derivative thereof, is included in a pharmaceutical composition for treating a patient in need from a bone disease, injury, or defect. In another embodiment, a therapeutically effective amount of a compound described herein, such as salubrinal, or an analog or derivative thereof, is used in the manufacture of a medicament for treating a patient in need from a bone disease, injury, or defect.

BRIEF DESCRIPTION OF THE DRAWINGS

FIG. 3. Tibial sections of proximal samples. The labels are: medial (m), lateral (l), and posterior surface (p). White bar=200 µm. The visible interior white lining in the loading group is indicative of new bone formation in excess of control.

FIG. 13. Upregulation of eIF2α-p in response to salubrinal. (A) Elevated eIF2α-p in response to 10 μM salubrinal for 5 h. (B) Elevated eIF2α-p in response to 10 or 50 μM salubrinal for 1 or 2 days.

FIG. 16. Micro CT images (medial surface, coronary section, and cross-section) of rat tibiae with surgical holes. Bar=1 mm. (A) Vehicle control (V) and salubrinal treated (T) tibiae 10 days after surgery. (B) Vehicle control (V) and salubrinal treated (T) tibiae 20 days after surgery.

FIG. 19. Micro CT images of the rat femurs with surgical holes. Bar=1 mm. (A) & (B) Vehicle control (V) and salubrinal treated (T) femurs 10 and 20 days after surgery. The anterior holes and their coronary sections are shown. (C) & (D) Vehicle control (V) and salubrinal treated (T) femurs 20 days after surgery. The posterior holes and their coronary sections are shown. (E) Cross sections of the vehicle control (V) and salubrinal treated (T) femurs 10 days after surgery. (F) Cross sections of the vehicle control (V) and salubrinal treated (T) femurs 20 days after surgery.

FIG. 22. (A) Section for CT imaging. (B) Control femoral head. (C) Infarcted femoral head after 48 h; M=metaphysis and E=epiphysis.

DETAILED DESCRIPTION

Figure 1:
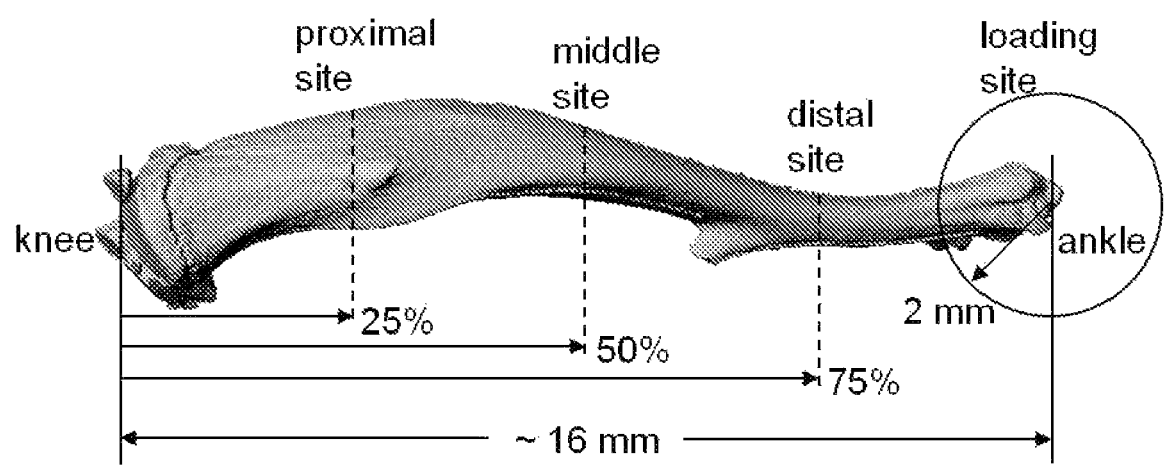
FIG. 1. Location of three cross-sections analyzed in histomorphometry.

In one illustrative embodiment, methods and compositions for treating a bone disease or defect are described herein. The methods comprise the step of administering to a patient in need of relief from the bone disease or defect a therapeutically effective amount of one or more inhibitors of phosphatase complexes that dephosphorylate one or more eukaryotic translation initiation factors wherein the factor is a factor 2 subunit alpha (eIF2α).

In another embodiment, methods and compositions for treating a bone disease or defect are described herein. The methods comprise the step of administering a therapeutically effective amount of one or more inhibitors of phosphatase complexes that dephosphorylate one or more eukaryotic translation initiation factors, wherein the factor is an eIF2α, to a patient in need of relief from the bone disease or defect, wherein the bone disease includes, but is not limited to, one or more of the conditions caused by osteoporosis, osteopenia, osteomalacia, porotic hyperostosis, osteogenesis imperfecta, osteitis fibrosa cystica, Wolcott-Rallison Syndrome, Synovial Cell Hyperplasia and Bone Destruction, IBMPFD, Marfan Syndrome, and the like.

In another illustrative embodiment, methods and compositions for treating a bone disease or defect are described herein. The methods comprise the step of administering a therapeutically effective amount of one or more inhibitors of phosphatase complexes that dephosphorylate one or more eukaryotic translation initiation factors, wherein the factor is an eIF2α, to a patient in need of relief from the bone disease or defect, wherein the affected bone includes, but is not limited to, such bones as those of the hip, thigh, shin, calf, foot, pelvis, spine, hand, wrist, forearm, arm, shoulder, neck, ribcage, and the like.

In another illustrative embodiment, methods and compositions for treating a bone fracture are described herein. The methods comprise the step of administering a therapeutically effective amount of one or more inhibitors of phosphatase complexes that dephosphorylate one or more eukaryotic translation initiation factors, wherein the factor is an eIF2α, to a patient in need of healing from the bone fracture, wherein the bone fracture includes, but is not limited to, simple, wedge, or complex fractures and the like, or fractures that are proximal, diaphyseal, or distal and the like.

In another embodiment, methods and compositions for increasing bone mineral density and/or bone mineral content in vivo are described.

It is appreciated that in each of the methods described herein, any one of or combination of the compounds described herein may be administered.

In another illustrative embodiment, described herein are compounds, compositions, and methods capable of up-regulating at least one of the genes ATF4, ATF3, osteocalcin (OCN), CHOP, or Runx2, either directly or indirectly. It is to be understood that such upregulation may be directly or indirectly linked to the phosphorylation of eIF2α.

In another embodiment, described herein are methods for treating a bone disease or defect comprising the step of administering to a patient in need of relief from the bone disease or defect a therapeutically effective amount of a compound capable of up-regulating at least one of ATF4, ATF3, osteocalcin (OCN), CHOP, or Runx2. Without being bound by theory, it is believed herein that such methods may include phosphatase complexes that dephosphorylate one or more eukaryotic translation initiation factors, such as factor 2 subunit alpha (eIF2α), and wherein the compound protects against endoplasmic reticulum stress-induced apoptosis.

In another embodiment, methods and compositions for treating a bone disease or defect are described herein. The methods comprise the step of administering to a patient in need of relief from the bone disease or defect a therapeutically effective amount of one or more inhibitors of phosphatase complexes, wherein the inhibitor is capable of maintaining the phosphorylation at the endoplasmic reticulum of the cell, and wherein the inhibitor is capable of stabilizing the phosphorylation state of the endoplasmic reticulum of the cell.

It is to be understood that the methods described herein may be performed to prophylactically to treat a patient yet to be in need of relief, but prone to, likely to, and/or destined to be in need of relief. It is also to be understood that the methods described herein may be performed to treat an existing condition. In addition, it is understood that the methods described herein may be performed to treat an acute and/or chronic condition.

In another embodiment, a method for treating a bone disease or defect is described herein. This method includes the step of administering to a patient in need of relief from the bone disease or defect a therapeutically effective amount of one or more inhibitors of one or more phosphatase complexes, wherein the inhibitor is a salubrinal, or an analog or derivative thereof. It is to be understood that as used herein, the term "a salubrinal" refers to the family of compounds that includes the specific compound salubrinal along with analogs and derivatives thereof. In addition, it is to be understood that the term "a salubrinal" also refers to prodrugs of the specific compound salubrinal and any of such analogs and derivatives of the specific compound. In addition, it is to be understood that the term "a salubrinal" also refers to any and all morphological forms of the specific compound salubrinal and any of such analogs and derivatives of the specific compound. In addition, it is to be understood that the term "a salubrinal" also refers to hydrates and other solvates of the specific compound salubrinal and any of such analogs and derivatives of the specific compound.

In another embodiment, methods and compositions for treating a bone disease or defect are described herein, where the method includes the step of administering to a patient in need of relief from the bone disease or defect a therapeutically effective amount of one or more inhibitors of phosphatase complexes, wherein the inhibitor is a compound of formula (I)

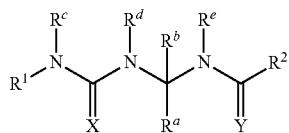

or a pharmaceutically acceptable salt thereof, wherein:

X and Y are independently O or S;

$R^1$ is alkyl, cycloalkyl, alkenyl, cycloalkenyl, aryl, or heteroaryl, each of which is optionally substituted;

$R^2$ is alkyl, cycloalkyl, alkenyl, cycloalkenyl, aryl, heteroaryl, cycloalkylalkyl, cycloalkenylalkyl, arylalkyl, heteroarylalkyl, cycloalkylalkenyl, cycloalkenylalkenyl, arylalkenyl, or heteroarylalkenyl, each of which is optionally substituted;

$R^a$ is optionally substituted alkyl;

$R^b$ is H or optionally substituted $C_1$-$C_6$ alkyl;

$R^c$, $R^d$, and $R^e$ are each independently selected from the group consisting of H, optionally substituted $C_1$-$C_6$ alkyl, acyl, or a prodrug capable of releasing the attached nitrogen in vivo to form the corresponding H or salt derivative thereof; and A and B are independently H, or optionally substituted $C_1$-$C_6$ alkyl.

In another embodiment, methods and compositions for treating a bone disease or defect are described herein, where the method includes the step of administering to a patient in need of relief from the bone disease or defect a therapeutically effective amount of one or more inhibitors of phosphatase complexes, wherein the inhibitor is a compound of formula (II)

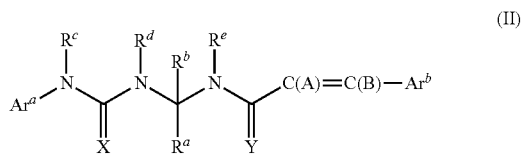

wherein, X and Y are independently O or S; $Ar^a$ and $Ar^b$ are independently aryl or heteroaryl, including bicyclic aryl or heteroaryl, each of which is optionally substituted with one or more substituents. Illustrative substituents include H, halo, nitrile, or optionally substituted $C_1$-$C_6$ alkyl, $C_1$-$C_6$ alkoxy, $C_1$-$C_6$ haloalkyl, $C_1$-$C_6$ haloalkoxy, aryl, aryloxy, heterocyclyl, heterocyclyloxy, fused aryl, fused heterocyclyl, and the like; $R^a$ is optionally substituted alkyl, such as haloalkyl; $R^b$ is H or optionally substituted $C_1$-$C_6$ alkyl; $R^c$, $R^d$, and $R^e$ are independently H, optionally substituted $C_1$-$C_6$ alkyl, or acyl; and A and B are independently H, or optionally substituted $C_1$-$C_6$ alkyl.

In another embodiment, methods and compositions for treating a bone disease or defect are described herein, where the method includes the step of administering to a patient in need of relief from the bone disease or defect a therapeutically effective amount of one or more inhibitors of phosphatase complexes, wherein the inhibitor is a compound of formula (III)

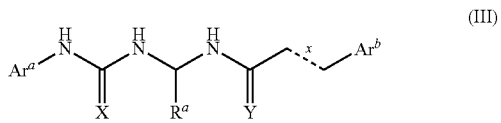

wherein bond x is either a single bond or a double bond; $R^a$ is optionally substituted alkyl, such as a haloalkyl; and $Ar^a$ and $Ar^b$ are each independently optionally substituted, and each independently selected from alkyl, cycloalkyl, aryl and heteroaryl, including fused or bicyclic heteroaryl.

In another embodiment, $R^a$=$CCl_3$, $CBr_3$, $CHCl_2$, $CH_2Cl$, and the like.

In another embodiment, $R^b$ is selected from the following illustrative structures:

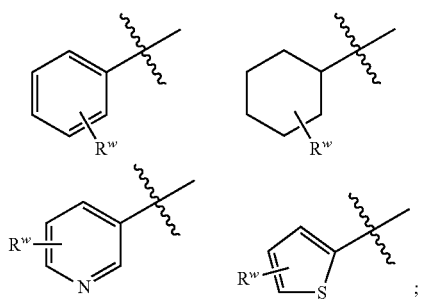

In another embodiment, $R^c$ is selected from the following illustrative structures:

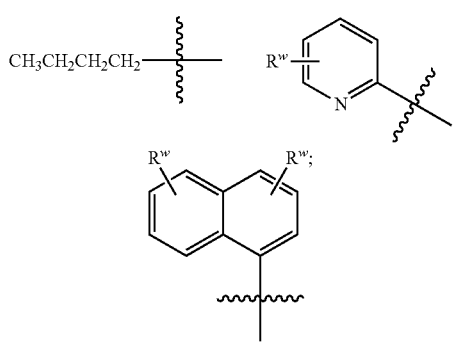

wherein $R^w$ is H or one or more substituents including alkyl, alkoxy, halo, haloalkyl, nitro, amino, cyano, and the like.

In another embodiment, bond x is a single bond. In another embodiment, bond x is a double bond. In another embodiment, bond x is a E-double bond.

In another embodiment, a method for treating a bone disease or defect is described herein. This method may comprise the step of administering to a patient in need of relief from the bone disease or defect a therapeutically effective amount of one or more inhibitors of one or more phosphatase complexes, wherein the inhibitor is a compound of formula (IV)

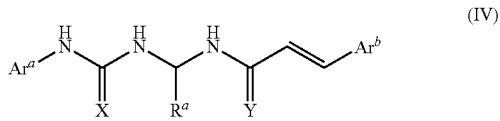

(IV)

wherein, X and Y are independently O or S, and wherein $Ar^a$ and $Ar^b$ are independently aryl or heteroaryl, including bicyclic aryl or heteroaryl, each of which is optionally substituted with one or more substituents. Illustrative substituents include H, halo, nitrile, or optionally substituted $C_1$-$C_6$ alkyl, $C_1$-$C_6$ alkoxy, $C_1$-$C_6$ haloalkyl, $C_1$-$C_6$ haloalkoxy, aryl, aryloxy, heterocyclyl, heterocyclyloxy, fused aryl, fused heterocyclyl, and the like. $R^a$ is optionally substituted alkyl, such as haloalkyl.

It is to be understood that in each of the foregoing compound embodiments described herein that variations are also described herein. For example, the selections for $Ar^a$ and $Ar^b$ are equally applicable to compounds of formula (II) as well as compounds of formula (III). Similarly, the selections for $R^a$ are equally applicable to compounds of any of formulae (I) to (IV). In addition, all possible combinations of the various embodiments described herein are also described. For example, in another embodiment, X is S and Y is O in each of formulae (I) to (IV). In another embodiment, Ra is haloalkyl in each of formulae (I) to (IV). In another embodiment, Ra is chloroalkyl in each of formulae (I) to (IV). In another embodiment, X is S and Y is O, and Ra is chloroalkyl in each of formulae (I) to (IV). In another embodiment, for compounds of formula (II), the following compounds are described where $Ar^a$ is optionally substituted heteroaryl, each of $R^b$, $R^c$, $R^d$, and $R^e$ are H, each of X and Y are independently O or S, and $Ar^b$ is optionally substituted phenyl.

In one illustrative aspect, the inhibitor of phosphatase complexes is a salubrinal, or an analog or derivative thereof, including, but not limited to, the heteroaryl compounds described herein, and analogs and derivatives wherein $Ar^a$ and $Ar^b$ are independently optionally substituted pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, and the like.

In another embodiment, methods and compositions for treating a bone disease or defect are described herein. These methods comprise the step of administering to a patient in need of relief from the bone disease or defect a therapeutically effective amount of one or more inhibitors of phosphatase complexes, wherein the inhibitor is a salubrinal. Illustratively, the salubrinal may be obtained from commercial sources, including, but not limited to, AXXORA LLC, ALEXIS BIOCHEMICALS, CALBIOCHEM, and the like. In another illustrative aspect, the salubrinal may be synthesized as described in the published literature, such as, for example, is described in Long, K., et al., "Structure-Activity relationship studies of salubrinal lead to its active biotinylated derivative," *Bioorganic & Medicinal Chemistry Letters*, 15:3849-3852 (2005), or by following other art-recognized synthetic methods.

For the treatment of bone diseases and fractures, illustratively the one or more inhibitors of phosphatase complexes described herein may be formulated in a therapeutically effective amount in conventional bone treatment dosage forms, including one or more carriers, diluents, and/or excipients. Such formulation compositions may be administered by a wide variety of conventional bone treatment routes in a wide variety of dosage formats, utilizing art-recognized products. See generally, Remington's Pharmaceutical Sciences, (16th ed. 1980). It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein.

The term "administering" as used herein includes systemic use, as when taken orally, parenterally (including by subcutaneous, intramuscular, intravenous and intrathecal routes), by inhalation spray, by nasal, rectal, or buccal routes, or topically in dosage form unit formulations containing conventional nontoxic pharmaceutically-acceptable carriers, adjuvants and vehicles. Suitable routes for parenteral administration include intravenous, intraarterial, intraperitoneal, epidurial, intraurethral, intrasternal, intramuscular and subcutaneous, as well as any other art recognized route of parenteral administration. Suitable means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The term "administering" as used herein also includes local use, as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated, such as is the case with bone diseases, injuries, or defects, that local administration may be directly in the bone marrow space, or locally in the surrounding tissue. Similar variations regarding local delivery to particular tissue types, such as organs, and the like, are also contemplated herein.

The term "therapeutically effective amount" includes a sufficient amount of the one or more inhibitors of phosphatase complexes described herein to treat the bone disease or defect at a reasonable benefit/risk ratio applicable to any medical treatment. However, it is to be understood that the total daily usage of the compounds and compositions described herein will be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known in the medical arts.

Depending upon the disease as described herein, the route of administration and/or whether the compounds and/or compositions are administered locally or systemically, a wide range of permissible dosages are contemplated herein, including doses falling in the range from about 1 μg/kg to about 1 g/kg. The dosages may be single or divided, and may administered according to a wide variety of protocols, including q.d., b.i.d., t.i.d., or even every other day, once a week, once a month, once a quarter, and the like. In each of these cases it is understood that the total daily, weekly, month, or quarterly dose corresponds to the therapeutically effective amounts described herein. When given locally, such as by injection near or at the site of injury, disease, or defect, illustrative doses include those in the range from about 1 μg/kg to about 10 mg/kg, or about 0.01 mg/kg to about 10 mg/kg, or about 0.01 mg/kg to about 1 mg/kg, or about 0.1 mg/kg to about 10 mg/kg, or about 0.1 mg/kg to about 1 mg/kg. When given locally, such as by injection near the site of injury, disease, or defect, or locally in tissues surrounding the site of injury, disease, or defect, illustrative doses include those in the range from about 0.01 mg/kg to about 10 mg/kg, or about 0.01 mg/kg to about 1 mg/kg, or about 0.1 mg/kg to about 10 mg/kg, or about 0.1 mg/kg to about 1 mg/kg. When given systemically, such as parenterally, illustrative doses include those in the range from about 0.01 mg/kg to about 100 mg/kg, or about 0.01 mg/kg to about 10 mg/kg, or about 0.1 mg/kg to about 100 mg/kg, or about 0.1 mg/kg to about 10 mg/kg. When given systemically, such as orally, illustrative doses include those in the range from about 0.1 mg/kg to about 1000 mg/kg, or about 0.1 mg/kg to about 100 mg/kg, or about 0.1 mg/kg to about 10 mg/kg, or about 1 mg/kg to about 1000 mg/kg, or about 1 mg/kg to about 100 mg/kg, or about 1 mg/kg to about 10 mg/kg.

In another illustrative embodiment, such as when treating a bone defect or fracture, or surgical wound, and the like, the inhibitor is administered parenterally locally q.d. at a dose of about 0.01 mg/kg, or about 0.05 mg/kg, or about 0.1 mg/kg, or about 0.5 mg/kg, or about 1 mg/kg, or about 5 mg/kg of body weight of the patient.

In another illustrative embodiment, such as when treating a systemic condition, such as osteoporosis, and the like, the inhibitor is administered parenterally systemically q.d. at a dose of about 0.1 mg/kg, or about 0.5 mg/kg, or about 1 mg/kg, or about 5 mg/kg, or about 10 mg/kg, or about 50 mg/kg of body weight of the patient.

In making the pharmaceutical compositions of the inhibitors of phosphatase complexes described herein, a therapeutically effective amount of one or more of the inhibitors in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

Described herein is also a method of preparation of the inhibitors of phosphatase complexes described herein. Illustratively, this method of preparation includes the step of reacting an amide with an aldehyde according to conventional procedures, followed by the step of amination of the resulting hydroxyl compound by activation of the hydroxyl group and displacement with an appropriate amine, and followed by the step of coupling of the resulting amine with an appropriate isocyanate or isothiocyanate to provide the desired product, as shown in the following scheme.

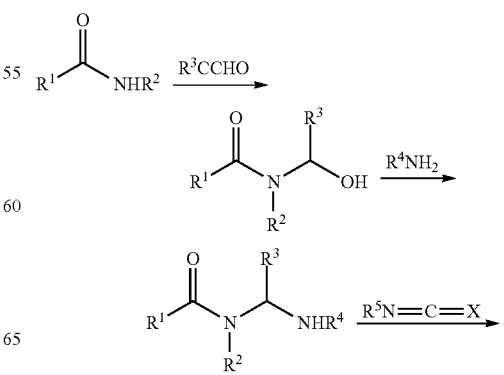

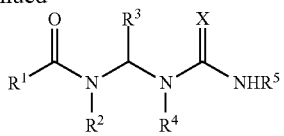

Exemplary of the method of preparation described herein is the procedure shown in the following scheme, wherein the amide, such as a cinnamide, is reacted with an aldehyde, such as chloral, and the hydroxyl group of the resulting intermediate is activated with a phosphorus pentahalide, for example, phosphorus pentachloride, and displaced with an amine to generate the corresponding amine, followed by coupling with an isothiocyanate, for example an arylisothiocyanate or heteroarylisothiocyanate, to produce the desired compound.

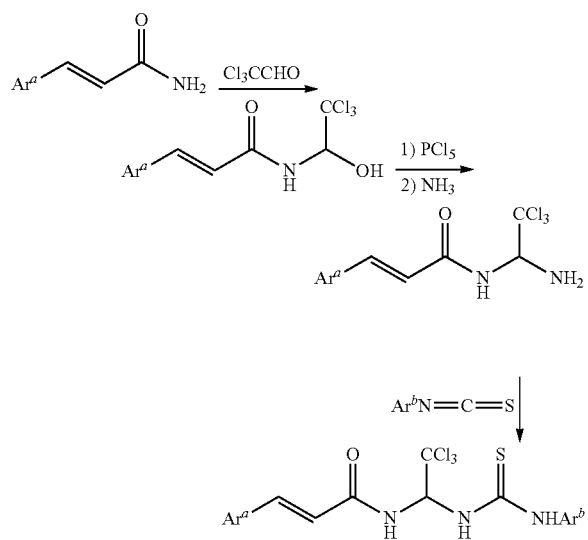

Additional examples of the preparation of the phosphatase inhibitors described herein may be found in the published literature, such as, for example, in Long et al., "Structure-Activity relationship studies of salubrinal lead to its active biotinylated derivative," *Bioorganic & Medicinal Chemistry Letters*, 15:3849-3852 (2005), or by following other art-recognized synthetic methods.

It is to be understood that the compositions containing the inhibitors of phosphatase complexes described herein may be co-administered to the patient together with other art-recognized treatments for bone diseases and bone fractures. Such other art-recognized treatments for bone diseases and fractures may include, but are not limited to, therapeutic agents such as bisphosphonates, including sodium alendronate (FOSAMAX), risedronate (ACTONEL), and ibandronate (BONIVA); the class of drugs called "dual action bone agents" (DABAs) such as strontium ranelate; teriparatide (FORTEO); denosumab (AMG 162); or co-administration in conjunction with hormone replacement therapy and/or vitamin D or calcium supplements; and the like.

In one embodiment, described herein is a pharmaceutical composition for treating a disease comprising an inhibitor of eIF2α dephosphorylation, wherein the inhibitor is present in a therapeutically effective amount for decreasing integrated stress response-induced apoptosis in a population of cells in vivo. In one aspect, the apoptosis is endoplasmic reticulum stress-induced apoptosis. In another aspect, the apoptosis is endoplasmic reticulum stress-induced apoptosis resulting in upregulation of one or more phosphorylases in the population of cells. In another aspect, the cell population comprises an osteoblast. In another aspect, the disease is a bone disease, injury, or defect, or a combination thereof. In another aspect, the inhibitor is capable of decreasing endoplasmic reticulum stress-induced apoptosis. In another aspect, the inhibitor is capable of maintaining the phosphorylation at the endoplasmic reticulum of the cell below a level causing apoptosis. In another aspect, the inhibitor is capable of stabilizing the phosphorylation state of the endoplasmic reticulum of the cell below a level causing apoptosis. In another aspect, the inhibitor is salubrinal, or an analog or derivative thereof. In another aspect, the disease is selected from the group comprising osteopenia, a bone defect, a bone injury, a bone fracture, a bone injury arising from a surgical procedure, a spinal bone defect, osteonecrosis, and pediatric hip necrosis, and combinations thereof.

In another embodiment, described herein is the use of an inhibitor of eIF2α dephosphorylation in the manufacture of a medicament for treating a disease resulting from integrated stress response-induced apoptosis in a population of cells, where the medicament comprises the inhibitor in a therapeutically effective amount for decreasing the apoptosis. In one aspect, the apoptosis is endoplasmic reticulum stress-induced apoptosis. In another aspect, the apoptosis is endoplasmic reticulum stress-induced apoptosis resulting in upregulation of one or more phosphorylases in the population of cells. In another aspect, the cell population comprises an osteoblast. In another aspect, the disease is a bone disease, injury, or defect, or a combination thereof. In another aspect, the inhibitor is capable of decreasing endoplasmic reticulum stress-induced apoptosis. In another aspect, the inhibitor is capable of maintaining the phosphorylation at the endoplasmic reticulum of the cell below a level causing apoptosis. In another aspect, the inhibitor is capable of stabilizing the phosphorylation state of the endoplasmic reticulum of the cell below a level causing apoptosis. In another aspect, the inhibitor is salubrinal, or an analog or derivative thereof. In another aspect, the disease is selected from the group comprising osteopenia, a bone defect, a bone injury, a bone fracture, a bone injury arising from a surgical procedure, a spinal bone defect, osteonecrosis, and pediatric hip necrosis, and combinations thereof.

In another embodiment, described herein is a method for treating a disease resulting from integrated stress response-induced apoptosis in a population of cells, the method comprising the step of administering to a patient in need of relief a therapeutically effective amount of an inhibitor of eIF2α dephosphorylation, where the therapeutically effective amount is capable of decreasing the apoptosis. In one aspect, the apoptosis is endoplasmic reticulum stress-induced apoptosis. In another aspect, the apoptosis is endoplasmic reticulum stress-induced apoptosis resulting in upregulation of one or more phosphorylases in the population of cells. In another aspect, the cell population comprises an osteoblast. In another aspect, the disease is a bone disease, injury, or defect, or a combination thereof. In another aspect, the inhibitor is capable of decreasing endoplasmic reticulum stress-induced apoptosis. In another aspect, the inhibitor is capable of maintaining the phosphorylation at the endoplasmic reticulum of the cell below a level causing apoptosis. In another aspect, the inhibitor is capable of stabilizing the phosphorylation state of the endoplasmic reticulum of the cell below a level causing apoptosis. In another aspect, the inhibitor is salubrinal, or an analog or derivative thereof. In another aspect, the disease is selected from the group comprising osteopenia, a bone defect, a bone injury, a bone fracture, a bone injury arising from a surgical procedure, a spinal bone defect, osteonecrosis, and pediatric hip necrosis, and combinations thereof.

EXAMPLES

The following illustrative examples describe particular embodiments of the invention. However, these examples are illustrative only, and should not be construed to limit the scope of either the specification or the claims.

Example 1

Bone Histomorphometry with Ankle Loading—Development of ankle loading: In order to evaluate the effects of salubrinal with and without mechanical loading, an ankle loading modality was developed similar to elbow and knee loading (Yokota, H., et al., "Osteogenic potentials with joint loading modality," *J. Bone Miner. Metab.* 23:302-308 (2005); Zhang, P., et al., "Bone formation in mouse tibia with knee-loading modality," *J. Appl. Physiol.* 100:1452-1459 (2006); Zhang, P., et al., "Knee loading causes diaphyseal cortical bone formation in murine femurs," *BMC Musculoskelet Dis.* 73:1-12 (2006)), which is able to induce bone formation specifically in the tibia. In order to evaluate independent and combined effects of salubrinal, salubrinal is administered locally to the tibia. In ankle loading, the C57BL/6 mouse was placed in an anesthetic induction chamber to cause sedation and then mask-anesthetized using 1.5% isoflurane. The loading rod and the stator were in contact with the distal end of the left tibia (lateral and medial malleoli), and loads were applied 3 min/day for 3 consecutive days in the lateral-medial direction (FIG. 1). 0.5 N force (peak-to-peak) at 5 Hz was employed. The right hindlimb was used as a sham loaded control in which the right ankle was placed under the loading rod in the same procedure used for the left ankle without applying a voltage signal to the loader. On days 2 and 7 after the last loading, the mice were given an intraperitoneal injection of calcein (Sigma) at 30 μg/g body mass for histomorphometry.

Figure 2:
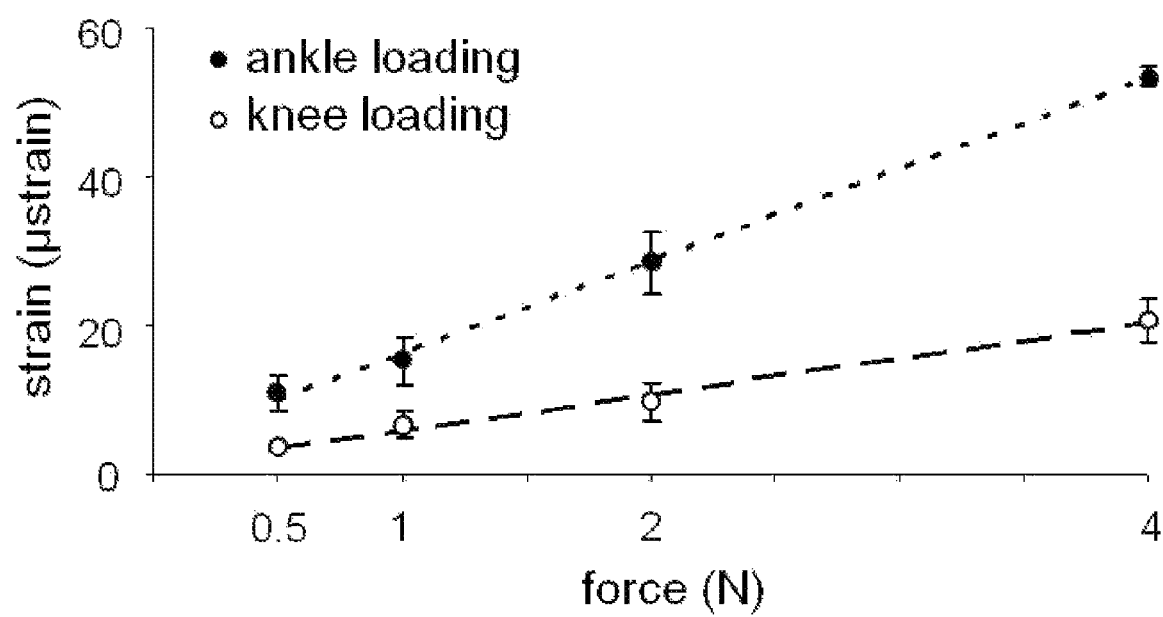
FIG. 2. Strain measurements with ankle and knee loading. Strain values as a function of loading force in N.

In a separate experiment, using a similar apparatus equipped with a strain gauge near the bone to be measured, the strain in the middle tibia was determined in response to ankle and knee loading using a strain gauge (0.7 mm in width and 2.8 mm in length; EA-06-015DJ-120, Measurements Group) (FIG. 2). The strain induced by ankle loading was approximately 2.6 times larger than that by knee loading, and it was 11±3 μstrains (0.5 N), 15±3 μstrains (1 N), 28±4 μstrains (2 N), and 54±1 μstrains (4 N). Additional details are described in Zhang et al., Bone 44:989-998 (2009).

Example 2

Figure 4:
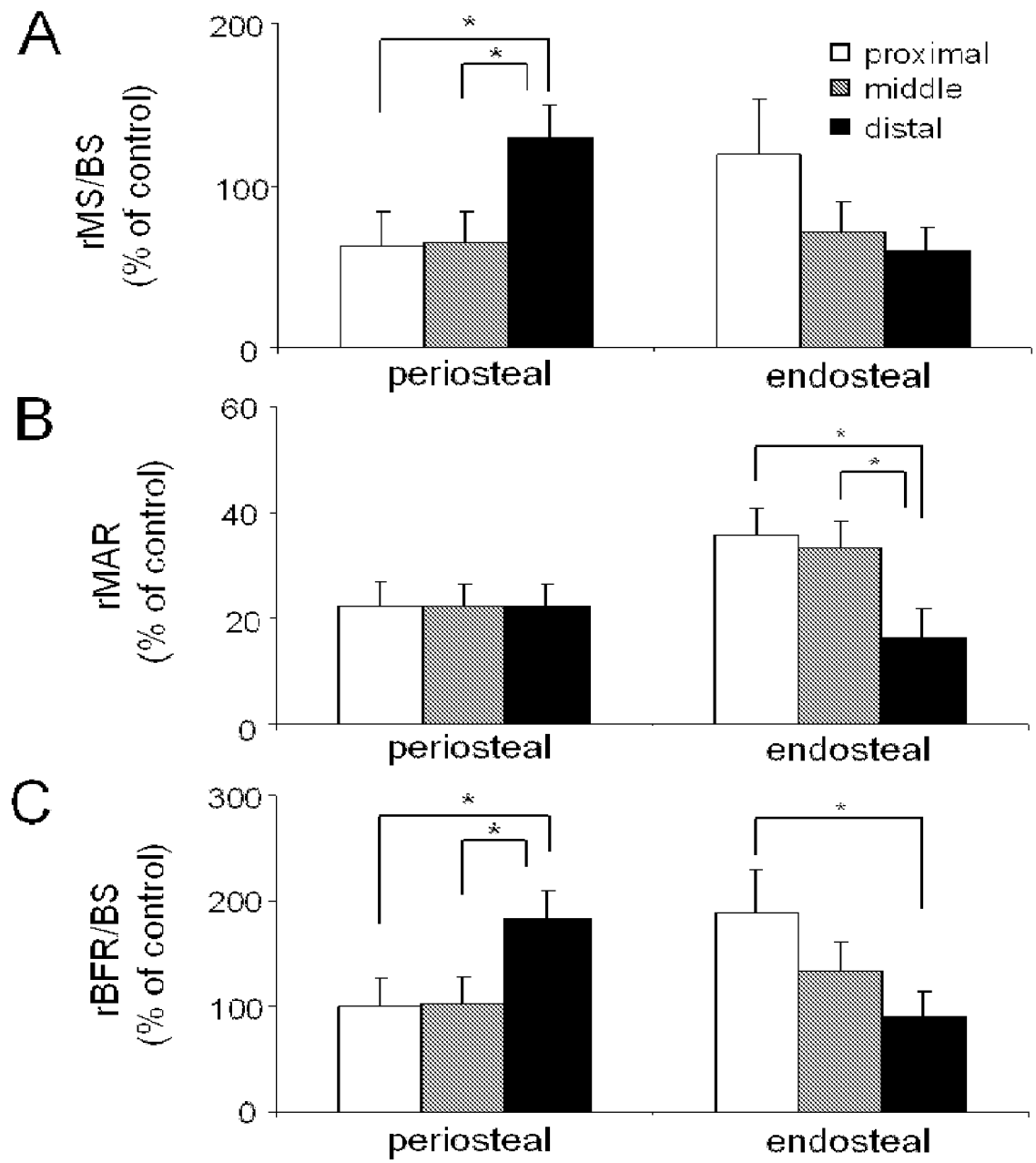
FIG. 4. (A) Increase in relative MS/BS (% of control); (B) Increase in relative MAR (% of control); (C) Increase in relative BFR/BS (% of control); (*=p<0.05).

Bone Histomorphometry with Ankle Loading—Bone histomorphometry: Ankle loading compared to control showed statistically significant elevated bone formation on both the periosteal and endosteal surfaces. In addition, load-driven bone formation was observed at all three cross-sections, and at both the loading site near the ankle and at the site away from the ankle (see, FIG. 1; Table 1). Compared to the nonloaded right tibia, an increase in relative mineralizing surface (rMS/BS), relative mineral apposition rate (rMAR), and relative bone formation rate (rBFR/BS) were determined and the percent change in three parameters was calculated (FIGS. 3-4).

TABLE 1

Increase in bone morphometric parameters with ankle loading [a]

| | | MS/BS (%) | fold change (p) [d] | MAR (μm/day) | fold change (p) [d] | BFR/BS (μm³/μm²/yr) | fold change (p) [d] |
|---|---|---|---|---|---|---|---|
| proximal section [b] | | | | | | | |
| periosteum | control | 16.76 ± 1.94 | 1.5 | 0.25 ± 0.01 | 1.2 | 16.01 ± 2.48 | 1.7 |
| | loading | 24.65 ± 3.19 | * | 0.30 ± 0.01 | *** | 26.77 ± 3.29 | * |
| endosteum | control | 55.67 ± 8.27 | 1.8 | 0.26 ± 0.01 | 1.4 | 53.61 ± 8.67 | 2.4 X |
| | loading | 97.52 ± 11.73 | ** | 0.35 ± 0.02 | *** | 127.52 ± 18.15 | *** |
| middle section | | | | | | | |
| periosteum | control | 45.17 ± 4.58 | 1.4 | 0.28 ± 0.01 | 1.2 | 47.23 ± 4.92 | 1.7 |
| | loading | 64.05 ± 4.57 | ** | 0.34 ± 0.01 | ** | 81.65 ± 7.52 | *** |
| endosteum | control | 30.41 ± 1.89 | 1.7 | 0.25 ± 0.01 | 1.3 | 28.09 ± 2.59 | 2.3 |
| | loading | 51.47 ± 6.83 | ** | 0.33 ± 0.01 | *** | 65.84 ± 11.86 | ** |
| distal section [c] | | | | | | | |
| periosteum | control | 23.15 ± 3.07 | 2.1 X | 0.25 ± 0.01 | 1.2 X | 23.36 ± 4.80 | 2.4 X |
| | loading | 47.60 ± 4.95 | *** | 0.31 ± 0.02 | * | 55.76 ± 7.80 | ** |
| endosteum | control | 31.79 ± 3.03 | 1.4 X | 0.25 ± 0.01 | 1.2 X | 30.09 ± 3.58 | 1.6 X |
| | loading | 45.64 ± 2.97 | ** | 0.29 ± 0.01 | * | 49.53 ± 4.60 | ** |

[a] mean ± s.e.m. (N = 15);
[b] near the knee;
[c] near the ankle;
[d] * = <0.05;  = <0.01; * = <0.001.

Example 3

Molecular Pathway Analysis with Ankle Loading—Stress responses (1 h) and anabolic responses (1 wk): In order to evaluate load-driven alterations in mRNA levels, real-time PCR was conducted using the loaded left tibiae and the control right tibiae. Reverse transcription was conducted with high capacity cDNA reverse transcription kits (Applied Biosystems), and quantitative PCR was performed using ABI 7500 with Power SYBR green PCR master mix kits (Applied Biosystems). First, one hour after last loading the mRNA levels of c-fos (6.7±0.7 fold), egr1 (4.0±1.1 fold), and ATF3 (4.6±1.0 fold) were upregulated. Second, 1 week after last loading the levels of Coll A, BMP2, osteopontin (OPN), osteocalcin (OCN) and bone sialoprotein (BSP) mRNAs were elevated. Transcription of ATF3 was influenced by ATF4 transcription factor (Gilchrist, M., et al., "Systems biology approaches identify ATF3 as a negative regulator of Toll-like receptor 4," *Nature* 441:173-178 (2006), but the level of ATF4 mRNA (1.0±0.2 fold) was not significantly elevated. Three mice showing elevated c-fos, egr1, and ATF3 were used for microarrays in Example 4.

Example 4

Molecular Pathway Analysis with Ankle Loading—Load-driven pathways in tibiae linked to PI3K, ECM, TGF-β, focal adhesion, and Wnt: In order to predict potential signaling pathways involved in ankle loading, pathway analysis was conducted using microarray-derived data and Pathway-Express software (Draghici, S., et al., "A systems biology approach for pathway level analysis," *Genome Res.* 17:1537-45 (2007). A total of 6 RNA samples were isolated with an RNeasy Plus mini kit (Qiagen) from 3 pairs of tibiae (mice a, b, and c—harvested 1 h after last loading from Example 3), and Agilent whole mouse genome arrays (G4112A) were employed. Data were filtered to remove background noise, and a modified t-test was performed to identify a group of genes that were altered >2-fold or <0.5-fold with statistical significance at p<0.01. Pathway-Express identified 5 potential pathways including phosphatidylinositol signaling (PI3K), ECM-receptor interaction, TGF-β signaling (Janssens, K., et al., "Transforming growth factor-beta1 to the bone," *Endocr. Rev.* 26:743-774 (2005)), focal adhesion (Tamura, Y., et al., "Focal adhesion kinase activity is required for bone morphogenetic protein—Smad 1 signaling and osteoblastic differentiation in murine MC3T3-E1 cells," *J. Bone Miner Res.* 16:1772-1779 (2001)), and Wnt signaling (Baron, R., et al., "Minireview: targeting the Wnt/β-catenin pathway to regulate bone formation in the adult skeleton," *Endocrinol.* 148:2635-2643 (2007)).

This study using mice indicates that ankle loading (0.5 N at 5 Hz for 3 min/day for 3 consecutive days) is capable of inducing bone formation in the tibia with potential activations of signaling pathways including PI3K, ECM-receptor, TGF-β, focal adhesion, and Wnt. This ankle loading model is used as a positive control of induction of bone formation for comparison with the compounds and compositions described herein.

Example 5

Figure 5:
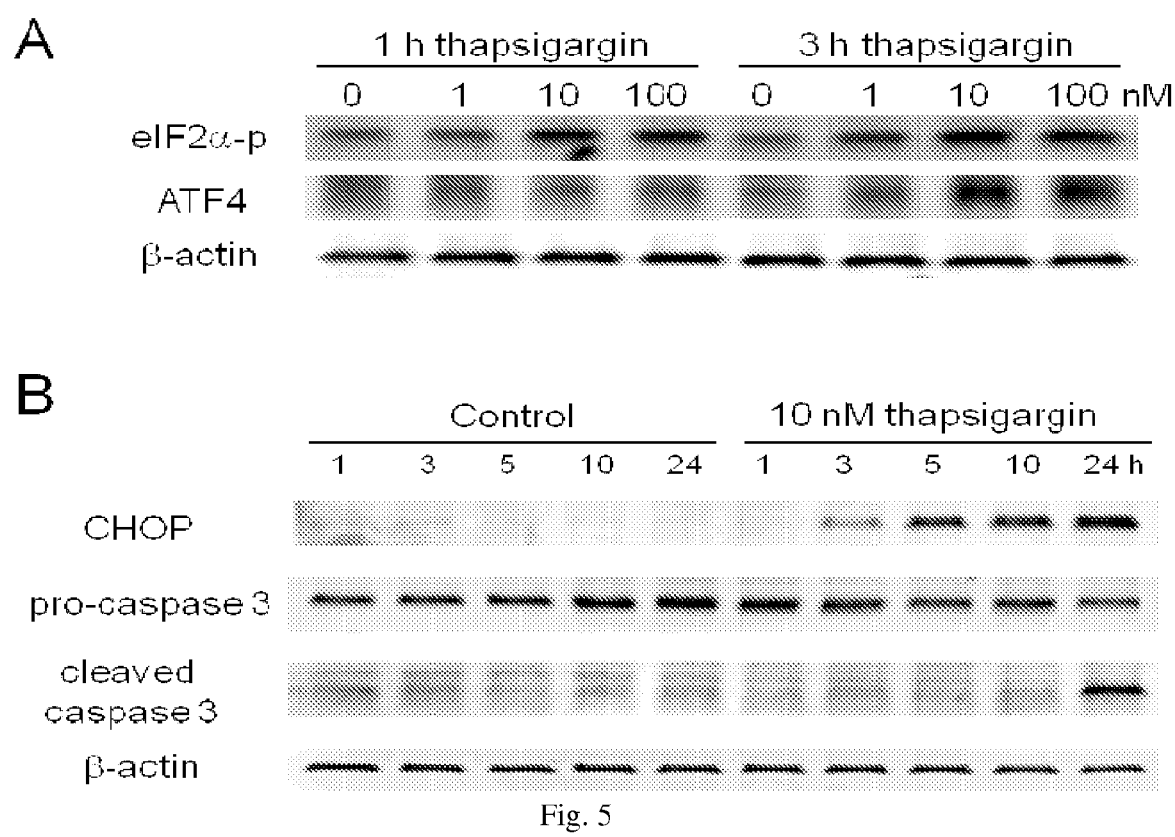
FIG. 5. Effects of thapsigargin on eIF2α-p and ATF4 protein. (A) Western blot for eIF2α-p and ATF4 proteins in response to 1-100 nM thapsigargin for 1, or 3 h; (B) CHOP, pro- and cleaved caspase 3 proteins in response to 10 nM thapsigargin.
Figure 6:
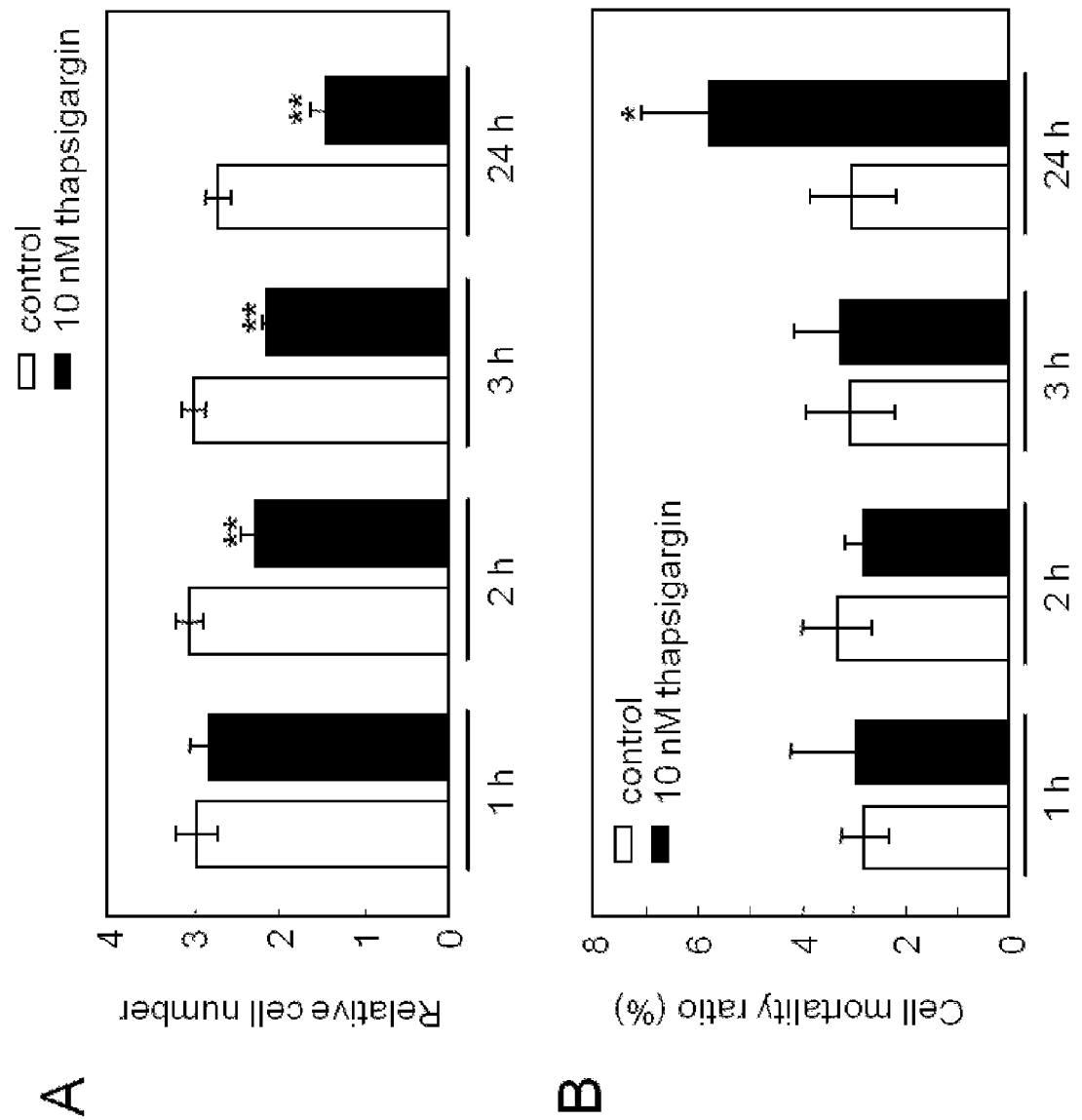
FIG. 6. Effects of thapsigargin on cell proliferation and death. (A) Normalized number of cells 24 h after exposure to 10 nM thapsigargin for 1, 2, 3, or 24 h; (B) Ratio of dead cells to the total cells in response to 10 nM thapsigargin for 1, 2, 3, or 24 h; (*=p<0.05; **=p<0.01).

Responses to Administration of Thapsigargin—Thapsigargin-induced effects on eIF2α-p, ATF4, and apoptosis: In order to evaluate the effects of thapsigargin on osteoblasts, a series of thapsigargin (Santa Cruz Biotech.) concentrations were employed to evaluate expression of phosphorylated eIF2α(eIF2α-p) and ATF4 proteins in MC3T3 E1 osteoblast-like cells (C4 clone) (Xiao, G., et al., "Ascorbic acid-dependent activation of the osteocalcin promoter in MC3T3-E1 preosteoblasts: requirement for collagen matrix synthesis and presence of an intact OSE2 sequence," *Mol. Endocrinol.* 11:1103-1113 (1997). At lower dosages below 0.1 nM, no detectable upregulation was observed (data not shown). At higher doses of 10 and 100 nM, the levels of eIF2α-p and ATF4 proteins were elevated (FIG. 5A). Thapsigarin is known to induce apoptosis when administered above a threshold concentration. To examine induction of apoptosis at 10 nM, the protein levels of CHOP (Marciniak, S. J., et al., "CHOP induces death by promoting protein synthesis and oxidation in the stressed endoplasmic reticulum," *Genes & Develop.* 18:3066-3077 (2006), pro-caspase 3 (inactive), and cleaved caspase 3 (active) were determined (FIG. 5B). The level of CHOP started to increase after 3 h and it became higher for a longer incubation (5, 10 and 24 h). Pro-caspase 3 level was not significantly altered, but the level of an active form was increased after 24 h. FIG. 6 shows the effects of 10 nM thapsigargin on cell proliferation and death. The results indicate that 1 h incubation with 10 nM thapsigargin (mild ER stress) does not alter the numbers of live and dead cells but longer incubation induces cell death.

Example 6

Figure 7:
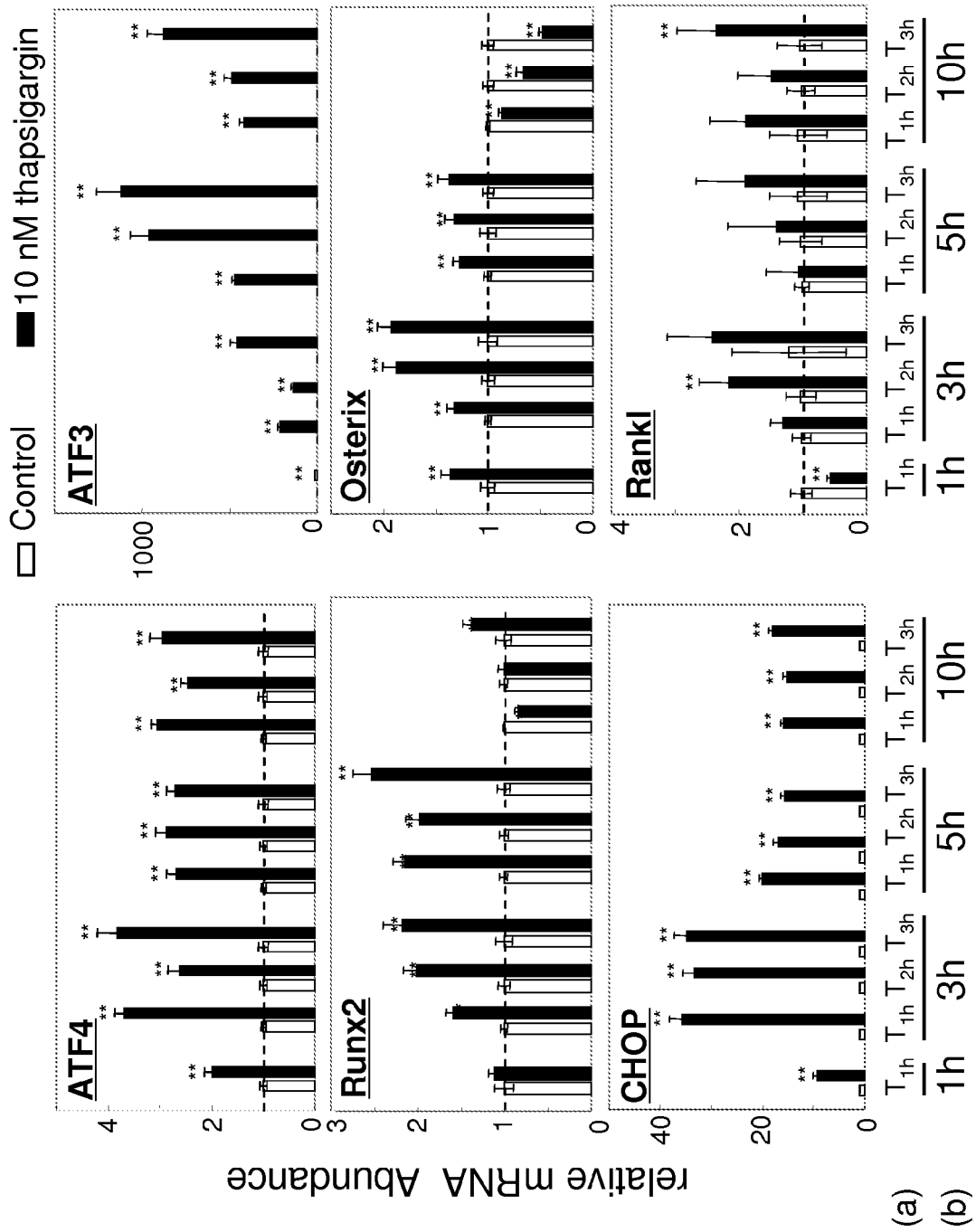
FIG. 7. Relative mRNA levels of ATF4, ATF3, Runx2, Osterix, CHOP, and Rank 1 in response to 10 nM thapsigargin for 1, 2, and 3 h exposures (T1h, T2h, and T3h, respectively). Osteoblast-like cells were harvested 1, 3, 5, or 10 h; (*=p<0.05; **=p<0.01); (a) indicates incubation time with 10 nM thapsigargin; (b) indicates harvest time.

Responses to Administration of Thapsigargin—Upregulation of transcription factors linked to bone formation as well as PERK: The effects of 10 nM thapsigargin on mRNA expression levels of ISR-linked genes (ATF4, ATF3, and CHOP) as well as genes involved in bone remodeling (Runx2, Osterix, and Rank 1), were examined (FIG. 7). In response to $T_{1h}$ (1 h exposure at 10 nM—mild ER stress), no significant difference in the cell number or mortality was observed between the control cells and the treated cells. Out of 4 transcription factors (ATF4, ATF3, Runx2, and Osterix), the level of ATF4 mRNA was elevated 2-4 fold throughout the treatments. ATF3 mRNA was upregulated 100-1000 times. An increase in Runx2 mRNA started at 3 h and peaked at 5 h, while Osterix mRNA was enhanced at 1 h. The mRNA level of CHOP was raised 10-35 fold, and Rank 1 mRNA was significantly up 3 h for $T_{2h}$ (2 h exposure at 10 nM) and 10 h for $T_{3h}$ (3 h exposure at 10 nM). The mRNA level of type 1 collagen was elevated 5 h and 10 h for $T_{1h}$ (1 h exposure at 10 nM).

Figure 8:
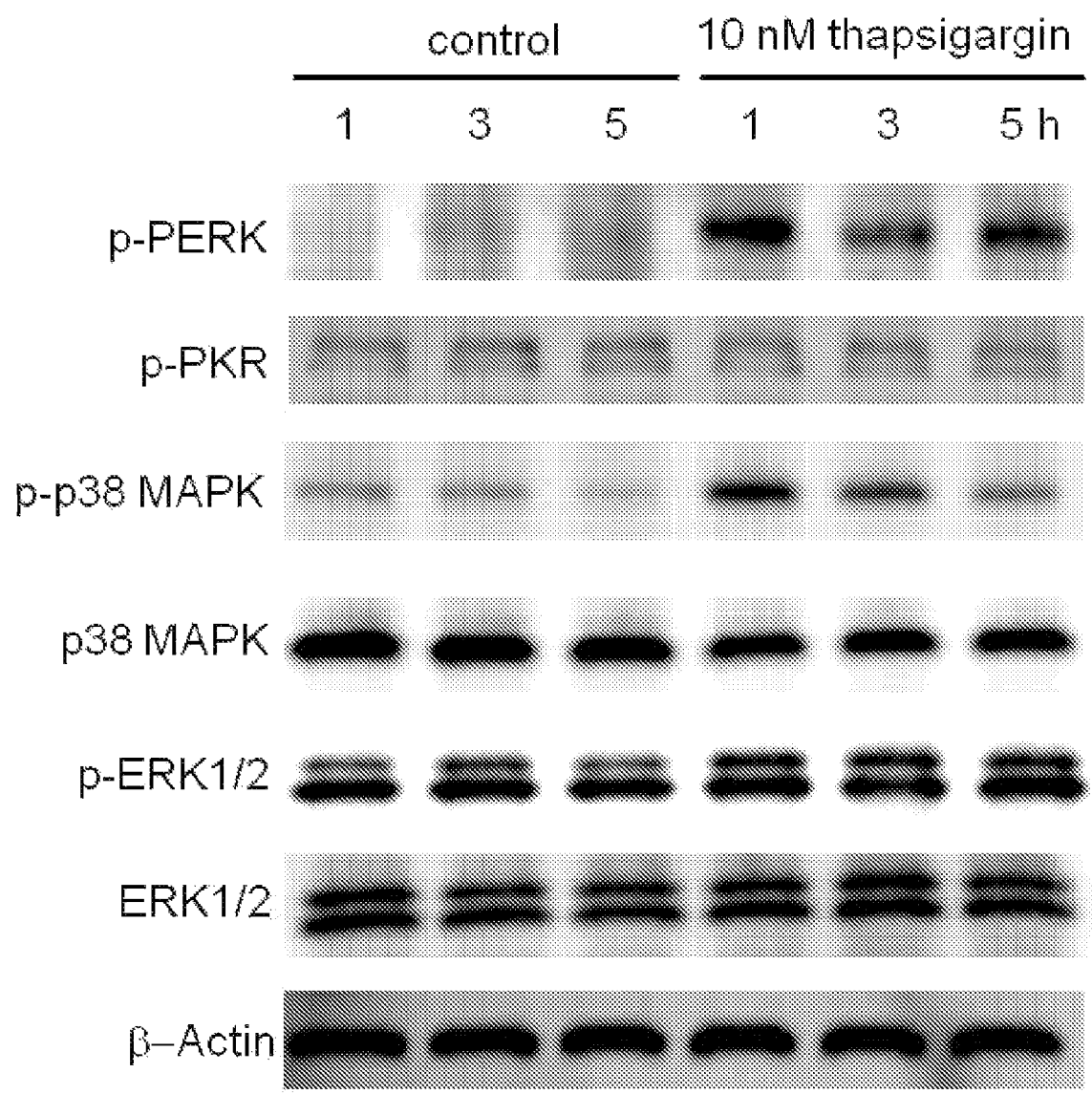
FIG. 8. Activation of phosphorylation of PERK and p-38 MAPK in response to 10 nM thapsigargin. The levels of p-PKR and p-ERK1/2 were unchanged.

In response to $T_{1h}$ (1 h exposure at 10 nM), the level of phosphorylation of two eIF2α kinases (PERK and PKR), and two MAP kinases (p-38 MAPK and ERK1/2) was examined (FIG. 8). The result revealed that 10 nM thapsigargin elevated the levels of p-PERK and p-p38 MAPK, but the levels of p-PKR and p-ERK1/2 were not altered.

Example 7

Responses to Administration of Thapsigargin—Linkage to hypoxia through microarray analysis: In response to thapsigargin-induced mild ER stress (1 h exposure at 10 nM), microarray experiments were conducted. First, Gene Set Enrichment Analysis (GSEA; Broad Institute) was used to identify a group of genes that shared common biological functions (Hamamura, K., et al., "Microarray analysis of thapsigargin-induced stress to the endoplasmic reticulum of mouse osteoblasts," *J. Bone Miner. Metab.* 26:231-240 (2008)). For each group of gene sets, GSEA calculates an enrichment score and evaluates statistical significance in the enrichment score. The microarray data exhibited similarity to the patterns in 68 gene sets (p<0.01) out of 1241 data sets in GSEA. Among those 68 gene sets, 7 gene sets had a false discovery rate smaller than 0.0001. Interestingly, 5 out of 7 gene sets were related to the responses to hypoxia or hypoxia inducible factor 1 (HIF1). The highest normalized enrichment score was given to the gene set, HYPOXIA_UP. All genes present in the array were reordered based on a ranked list-metric value (a mean expression ratio between the thapsigargin-treated and untreated samples), and the best enrichment score of "−0.66" was assigned. Note that if the expression ratio is random among the genes in HYPOXIA_UP, the expected enrichment score is ±0.23. The enrichment score, ranked isometric and P (enrichment score) supported the conclusions drawn from the software program output. The following core enrichment genes in HYPOXIA_UP were significantly upregulated upon treatment with thapsigargin compared to control:

| | | |
|---|---|---|
| BNLP3L | CEBPB | PFKFB3 |
| SLC2A3 | PPP1R3C | PLOD2 |
| JCFC1R1 | BHLHB3 | P4HA1 |
| EGLN1 | PBEF1 | MAFF |
| ALDOC | P4HA2 | ANKRD37 |
| WSB1 | ERO1L | STC2 |
| PPF1A4 | MXI1 | RORA |
| GBE1 | ENO2 | VEGF |
| JK2 | PDK1 | BHLHB2 |
| KLF4 | JMJD1A | BNIP3 |
| KLF7 | ATF3 | ADM |
| WDR54 | KLH24 | NDRG1 |

Figure 9:
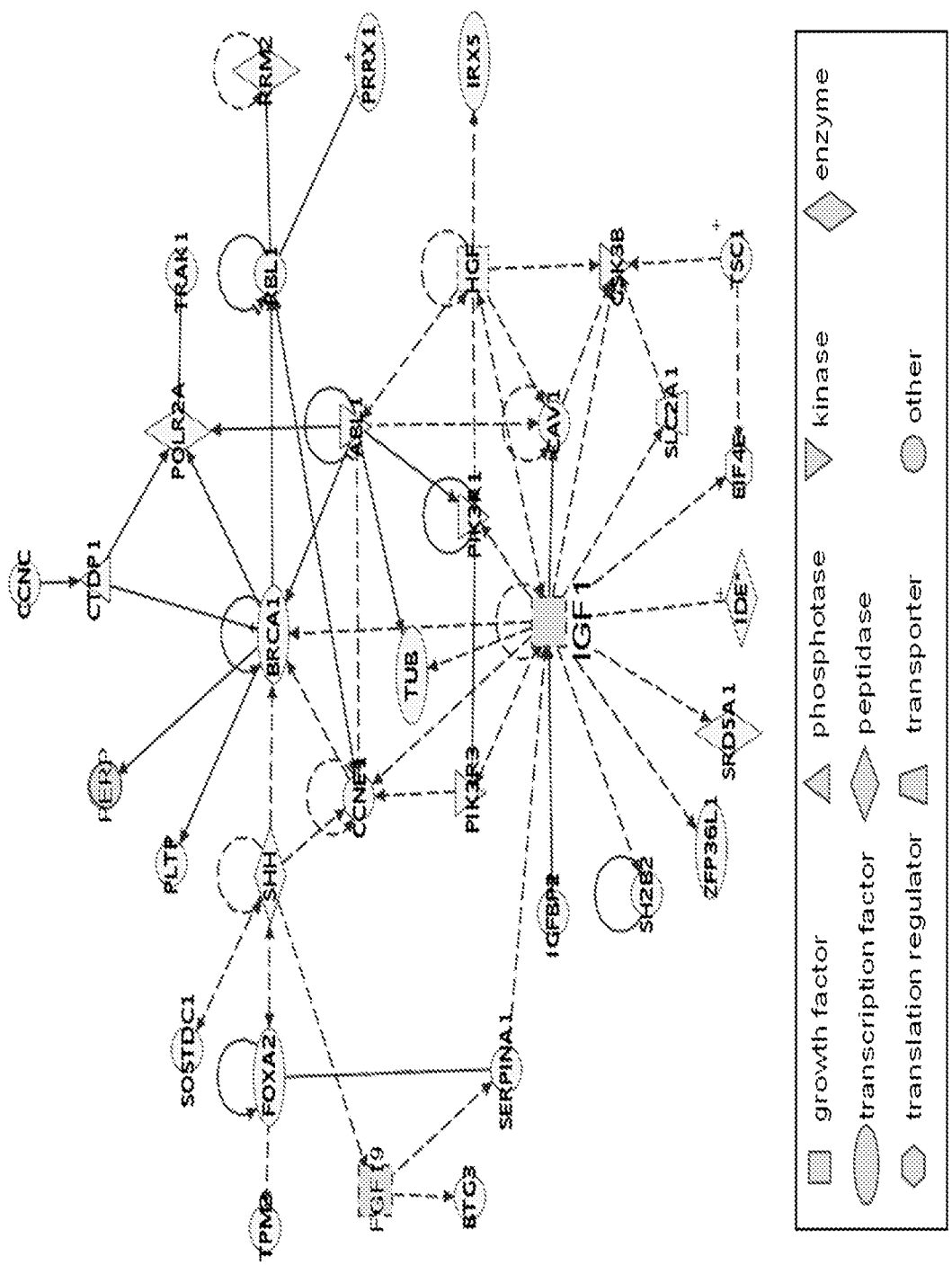
FIG. 9. Pathway I in response to 10 nM thapsigargin with Ingenuity Pathways Analysis (IPA). This pathway is identified as "connective tissue development and function."

Second, IPA (Ingenuity Pathways Analysis) was employed to predict potential linkages among various growth factors, transcription factors, kinases, etc. in response to 10 nM thapsigargin (Hamamura, K., et al., "Microarray analysis of thapsigargin-induced stress to the endoplasmic reticulum of mouse osteoblasts," *J. Bone Miner. Metab.* 26:231-240 (2008)). Two emerged pathways were "Pathway 1: connective tissue development and function" and "Pathway 2: organ morphology." In both pathways 35 genes in each of the networks were all affected by thapsigargin (100% match) with a score of 55, where a score of 3 or above are considered statistically significant. Pathway 1 included insulin-like growth factor 1 (IGF1) (FIG. 9), while ATF4 was included in Pathway 2 (data not shown).

Without being bound by theory, it is believed herein that this example using MC3T3 cells with thapsigargin indicates that mild induction of ER stress (1 h incubation at 10 nM thapsigargin) activates phosphorylation of PERK and alters expression levels of genes involved in hypoxia, connective tissue development, and organ morphology including ATF4 protein, HIF1 mRNA, and IGF1 mRNA.

Example 8

Figure 10:
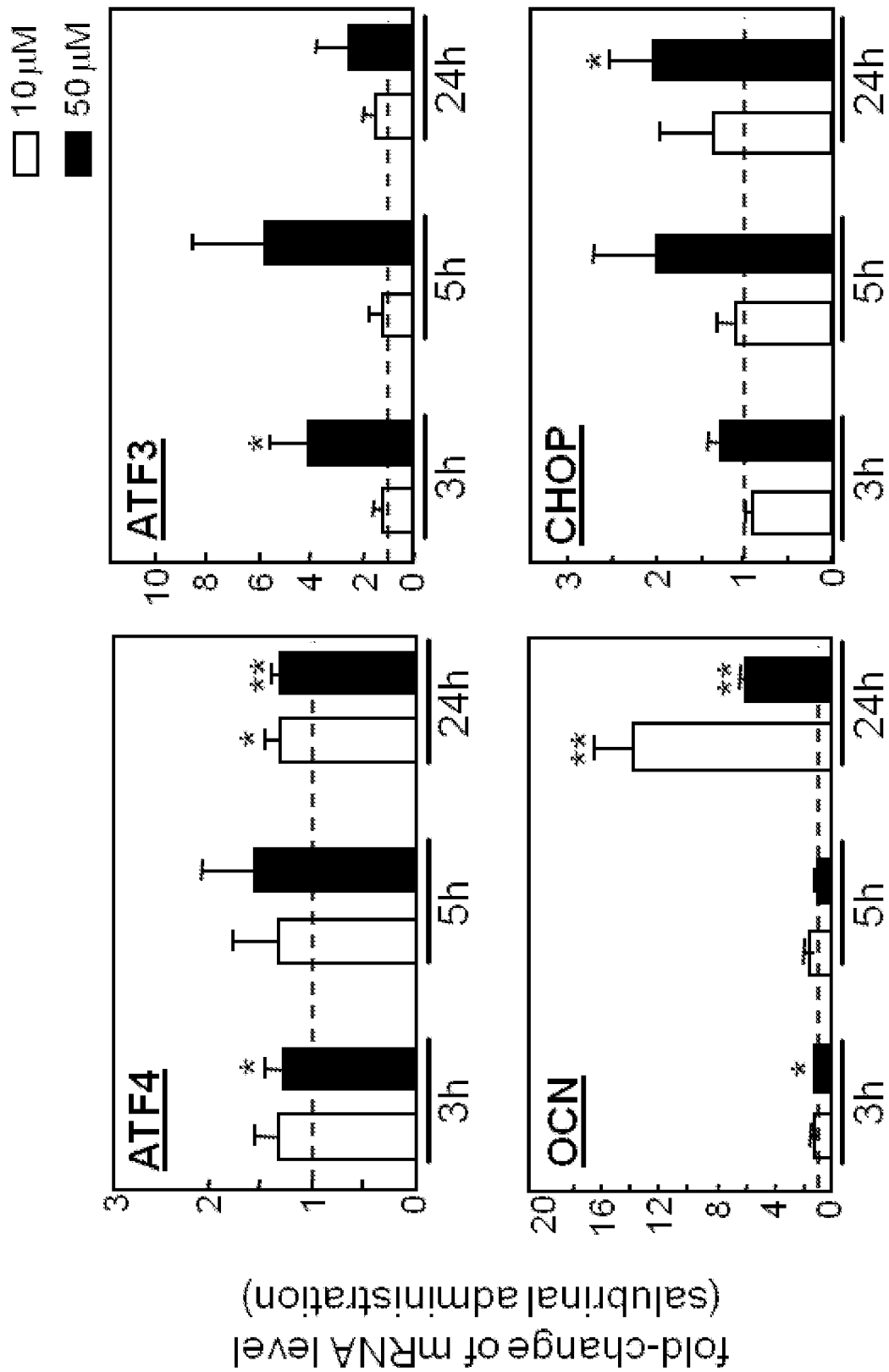
FIG. 10. Effects of salubrinal on mRNA expression levels of ATF4, ATF3, osteocalcin, and CHOP in MC3T3 cells.
Figure 11:
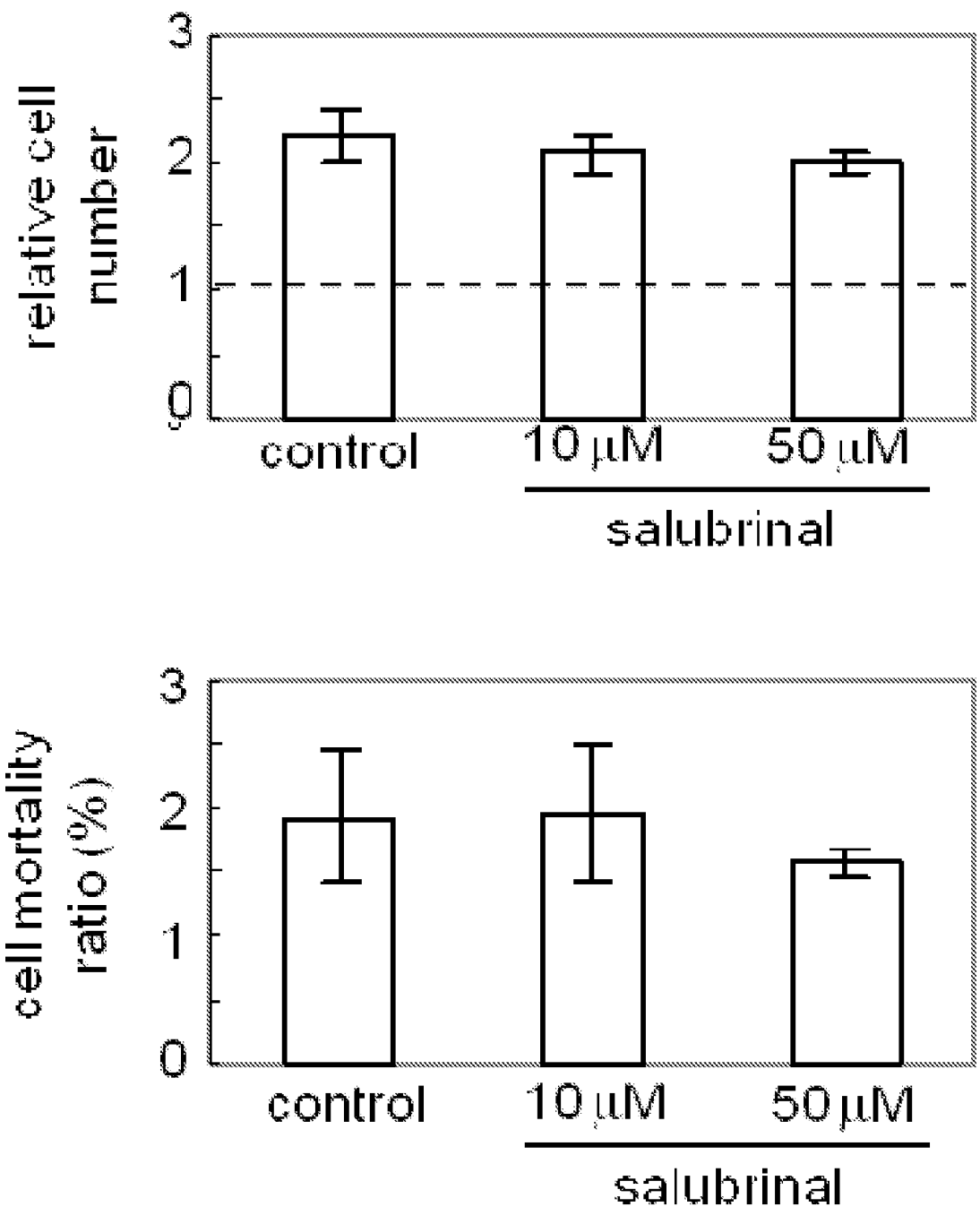
FIG. 11. Administration of 10 & 50 µM salubrinal for 24 h did not alter cell proliferation and death in MC3T3 cells.

Responses to Administration of Salubrinal—In vitro responses to salubrinal: In order to evaluate the effects of salubrinal, MC3T3 E1 osteoblast-like cells and MLO-A5 osteocyte cells (Barragan-Adjemian, C., et al., "Mechanism by which MLO-A5 late osteoblasts/early osteocytes mineralize in culture: similarities with mineralization of lamellar bone," *Calcif. Tissue Int.* 79:340-353 (2006)) were incubated with salubrinal at 100 nM-50 µM for 1-24 h. The mRNA levels of the selected genes, TF4, ATF3, Osteocalcin (OCN), and CHOP, were determined by real-time PCR. In MC3T3 cells, the mRNA levels for the selected genes were upregulated (FIG. 10; $*p<0.05$ and $**p<0.01$), while MLO-A5 cells did not show any significant alterations (data not shown). In MC3T3 cells, for instance, the Osteocalcin mRNA level, which is regulated by ATF4 and Runx2 (Xiao et al. 2005), was elevated 11.8±0.2 fold at 10 µM salubrinal in 24 h. Since the treatment with thapsigargin did not increase the level of Osteocalcin mRNA under any tested conditions (1-100 nM for 1-24 h), cellular responses to salubrinal and thapsigargin are considerably different in MC3T3 cells. Furthermore, salubrinal did not alter cell proliferation or death in MC3T3 cells at 10 or 50 µM for 24 h (FIG. 11), but thapsigargin induced apoptosis at 10 nM for 3 h or more incubation. On the contrary, incubation with 50 µM salubrinal reduced cell death, although no statistical difference was detected ($p>0.05$).

Example 9

Figure 12:
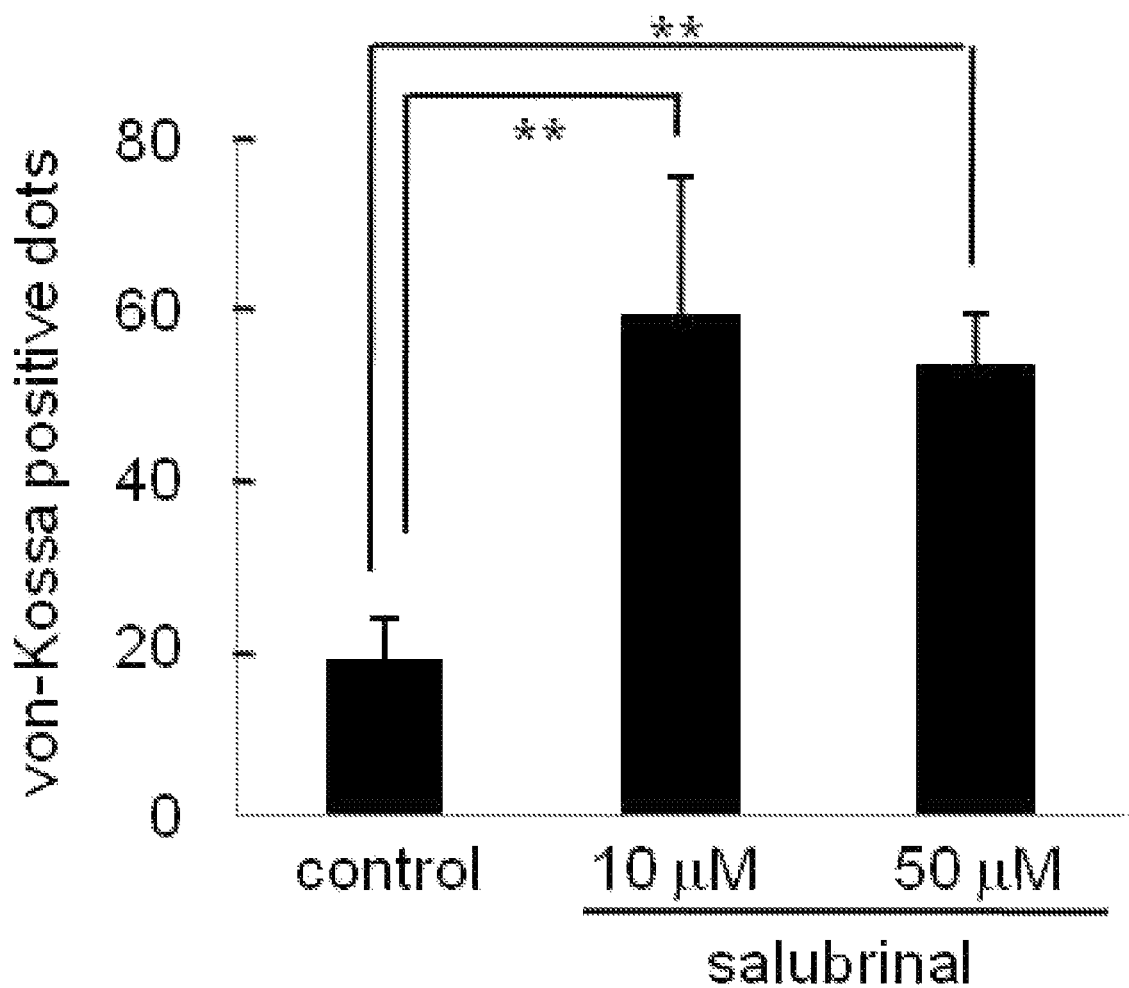
FIG. 12. von Kossa staining for control MC3T3 cells and 10 µM salubrinal treated cells showing number of stained dots.

To evaluate the effects of salubrinal on mineralization, MC3T3 cells were grown in the presence of 50 µg/ml of ascorbic acid and 5 mM β-glycerophosphate for 10 days with and without 10 or 50 µM salubrinal, and von-Kossa staining was conducted. Cells were fixed in 10% formalin and incubated in 5% silver nitrate for 30 min. After rinsing in PBS, staining was developed in 5% sodium carbonate for 2 min. They were counterstained with 0.1% nuclear fast red solution. The results showed that both the treatment with 10 and 50 µM salubrinal increased the number of von-Kossa positive dots. In the field-of-view with 10× objective lens, the mean number of positive dots was 3.2-fold (10 µM salubrinal) and 2.9-fold (50 µM salubrinal) more than that for control cells without salubrinal treatment (FIG. 12).

Example 10

MS3T3 osteoblast-like cells were used to evaluate the level of eIF2α-p (phosphorylated form of eukaryotic initiation factor 2—subunit α) in response to salubrinal. Western analysis revealed that administration of salubrinal at 10 µM or 50 µM for both the period of 1 to 5 h and the period of 1 to 2 days elevated the phosphorylated level of eIF2α (FIG. 13).

Example 11

Responses to Administration of Salubrinal—In Vivo Responses to salubrinal: In order to evaluate the effects of salubrinal in vivo, salubrinal was injected into an intramedullary cavity of the left femora of C57BL/6 mice and alterations in bone mineral density (BMD) and bone mineral content (BMC) were determined. There were 9 salubrinal treated mice as well as 9 placebo mice (injection of PBS). All mice received 4 injections of either salubrinal or PBS in the left femur, while the right femur was used as contralateral control. In four consecutive injections with a 0.5-inch #26-gauge needle and a Hamilton micro-syringe, the lateral side was used on the $1^{st}$ and $3^{rd}$ injections and the medial side on the $2^{nd}$ and $4^{th}$ injections. An injection volume was 20 µl for salubrinal or PBS, and the salubrinal concentration was 50 µM. Prior to the $1^{st}$ injection, the mean body weight for the two groups was not significantly different (18.28±0.33 g for Salubrinal group and 18.25±0.32 g for Placebo group). At the time of harvest (2 wks after the $1^{st}$ injection), an increase in body weight in Salubrinal group (0.80±0.13 g) was higher than that in Placebo group (0.28±0.15 g; $p<0.05$). Harvested bone samples were analyzed with PIXImus (version 1.4, GE Medical System Lunar) for determination of BMD and BMC.

Figure 14:
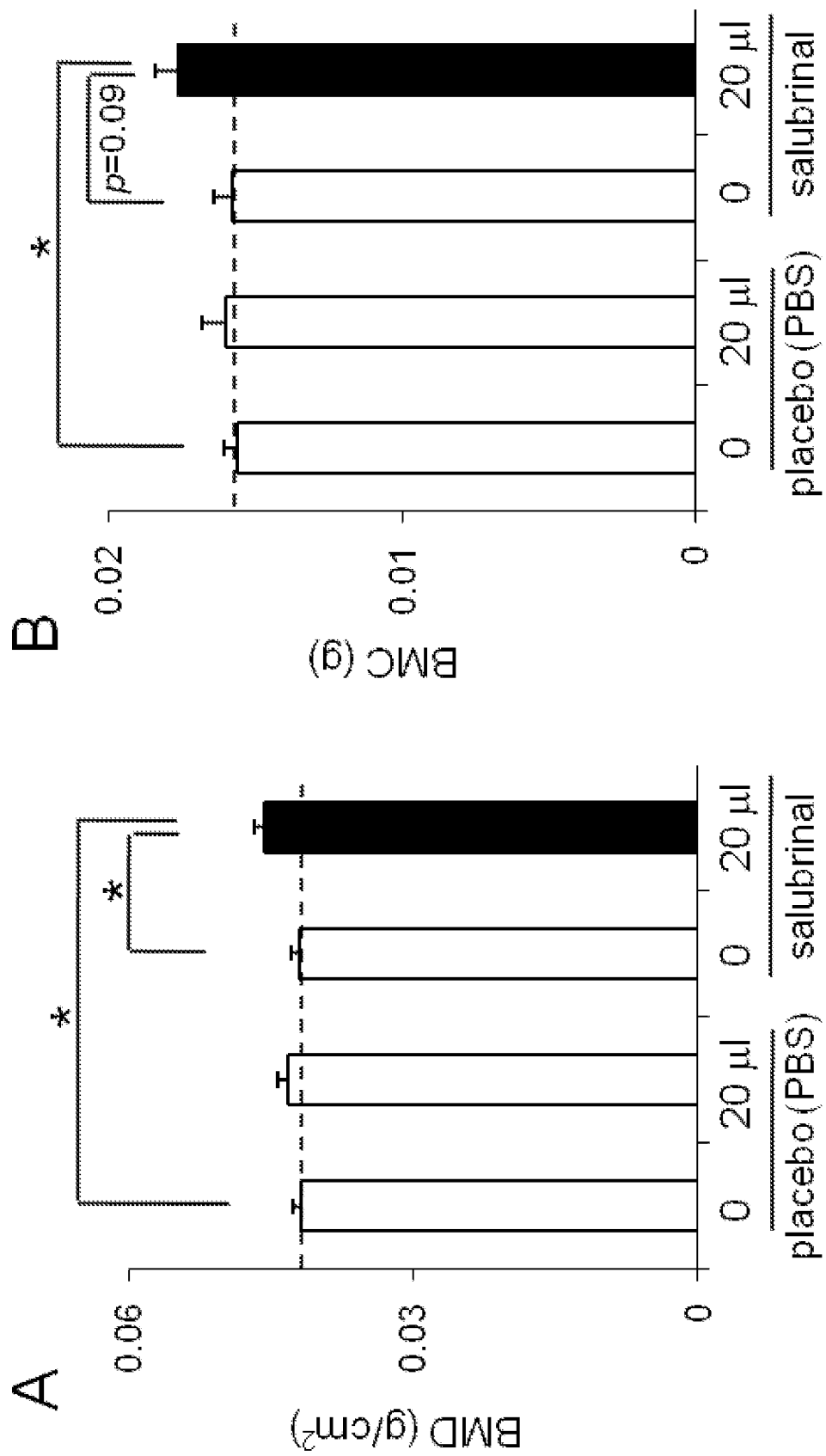
FIG. 14. Effects of salubrinal in vivo. Placebo group received 20 μl injection of PBS in the left femur and no treatment in the right femur. Salubrinal group received 20 μl injection of salubrinal (50 μM) in the left femur and no treatment in the right femur. The number of mice in each group was 9. The asterisk indicates $p<0.05$, and the values for mean±s.e.m. are shown. (A) Increased bone mineral density (BMD) by salubrinal injection. (B) Increased bone mineral content (BMC) by salubrinal injection.

The results revealed that, compared to the contralateral control, salubrinal injection increased BMD ($p=0.02$) and showed a trend to elevate BMC ($p=0.09$) (FIG. 14). However, in placebo group no statistically significant change was detected by injection of PBS: BMD values in $g/cm^2$ were: 0.0417±0.0010 (no injection in contralateral control placebo group; mean±s.e.m.); 0.0431±0.0012 (20 µl PBS injection in placebo group); 0.0419±0.0001 (no injection in contralateral control salubrinal group); and 0.0456±0.0011 (20 µl salubrinal injection in salubrinal group).

Without being bound by theory, it is believed herein that these Examiner indicate that in M3T3 cells administration of salubrinal increases Osteocalcin mRNA level and promotes von Kossa staining; and in C57BL/6 mice BMD was significantly elevated in the salubrinal-administered femur.

Example 12

Figure 15:
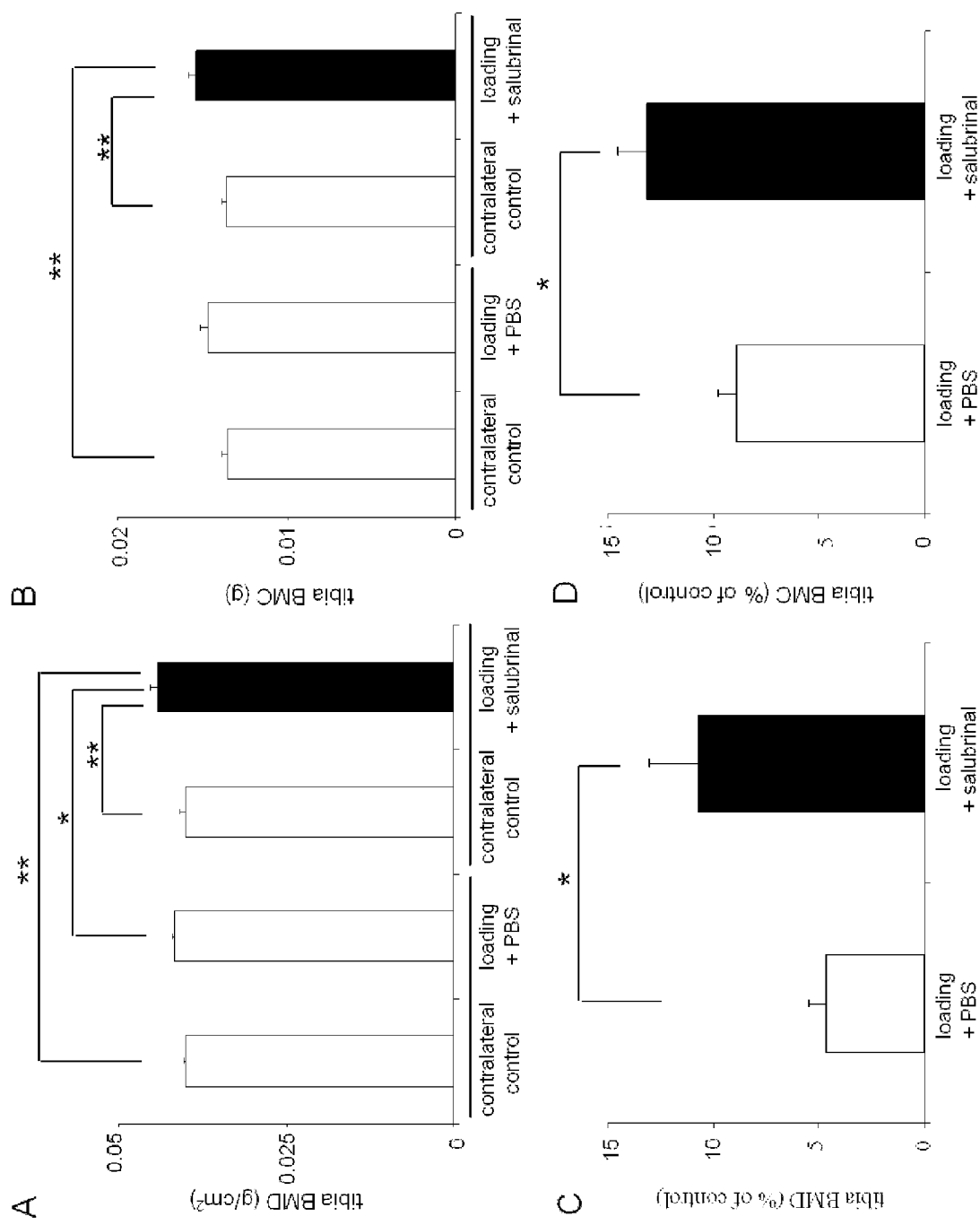
FIG. 15. Combined effects of ankle loading and salubrinal; (*=$p<0.05$ and **=$p<0.01$). (A) Tibia BMD. (B) Tibia BMC. (C) % increase in tibia BMD by "loading alone" and "loading plus salubrinal." (D) % increase in tibia BMC by "loading alone" and "loading plus salubrinal."

Mouse tibia-bone formation: Twenty C57/BL/6 Female Mice (~8 weeks, body weight~18 g) were employed to examine the combined effects of ankle loading and local administration of salubrinal to the tibia (Zhang P, et al., Salubrinal stimulates anabolic responses in mouse femora, 55th Ann Meeting ORS (2009)). Local administration was targeted into a bone marrow cavity from the proximal tibia. A total volume of 20 μl PBS was injected to the left hindlimb with or without 0.025 mg/kg (100 μM) salubrinal (Calbiochem) using a micro-syringe with a 0.5-inch #26-gauge needle (Worsham D N, et al., In vivo gene transfer into adult stem cells in unconditioned mice by in situ delivery of a lentiviral vector, Mol. Ther. 14:514-24 (2006); Zhu Y, et al., eIF-2α protects brainstem motoneurons in a murine model of sleep apnea, J. Neurosci. 28:2168-78 (2008)). In examination of the combined effects of mechanical loading and salubrinal administration, ankle loading was given for 5 consecutive days after administration of salubrinal on each day. The mouse was placed in an anesthetic induction chamber to cause sedation and then mask-anesthetized using 1.5% isoflurane. With a custom-made piezoelectric mechanical loader, loads were applied to the left ankle for 5 min/day in the lateral-medial direction. The loading frequency was 5 Hz, and the peak-to-peak force was 0.5 N (FIG. 15). The right hindlimb was used as a sham-loaded control (Zhang P, et al., Joint loading-driven bone formation and signaling pathways predicted from genome-wide expression profiles, Bone 44:989-998 (2009)).

With local administration of salubrinal and ankle loading, the additive effects on BMD and BMC were observed in the mouse tibia (FIG. 15). Compared to contralateral controls, the simultaneous salubrinal/loading treatment increased BMD ($0.0400\pm0.0008$ g/cm$^2$ in control and $0.0443\pm0.0011$ g/cm$^2$ in salubrinal; $p<0.01$), and BMC ($0.0136\pm0.0003$ g in control and $0.0154\pm0.0004$ g in salubrinal; $p<0.01$). Compared to the vehicle control group with ankle loading, the salubrinal group with ankle loading increased BMD from $0.0418\pm0.0003$ g/cm$^2$ to $0.0443\pm0.0011$ g/cm$^2$ ($p<0.05$). The relative increases in BMD and BMC with ankle loading and salubrinal injection was 2.3 and 1.5 fold higher than those with ankle loading alone, respectively (both $p<0.05$).

Example 13

Rat tibia—healing of surgical wounds. Twenty female SD rats (~8 weeks, body weight~180 g) received a surgical hole with ~2.0 mm in diameter in the left and right tibiae (Zhang P., et al., Knee loading accelerates bone healing in mice, J. Bone Miner. Res. 22:1979-1987 (2007)). The hole was located on the medial surface ~15 mm distant apart from the proximal end of the tibia (Chiba S., et al., Molecular analysis of defect healing in rat diaphyseal bone, J. Vet. Med. Sci. 63:603-606 (2001)). During the first 5 days, 100 μl of salubrinal solution at dosage of 0.025 mg/kg was injected into the left limb and a PBS solution (vehicle control) in the right limb (Wang J W, et al., Locally applied simvastatin promotes fracture healing in ovariectomized rat, Osteoporosis Int. 18:1641-1650 (2007)). Injection was subcutaneous targeted to the wound site. Rats were sacrificed on days 10 or 20 after surgery, and the axial and transverse length of the holes as well as cortical thickness (1.5 mm proximal and distal to the center of the hole) were determined with micro CT imaging (μCT-20, Scanco Medical AG) (FIG. 16).

Figure 17:
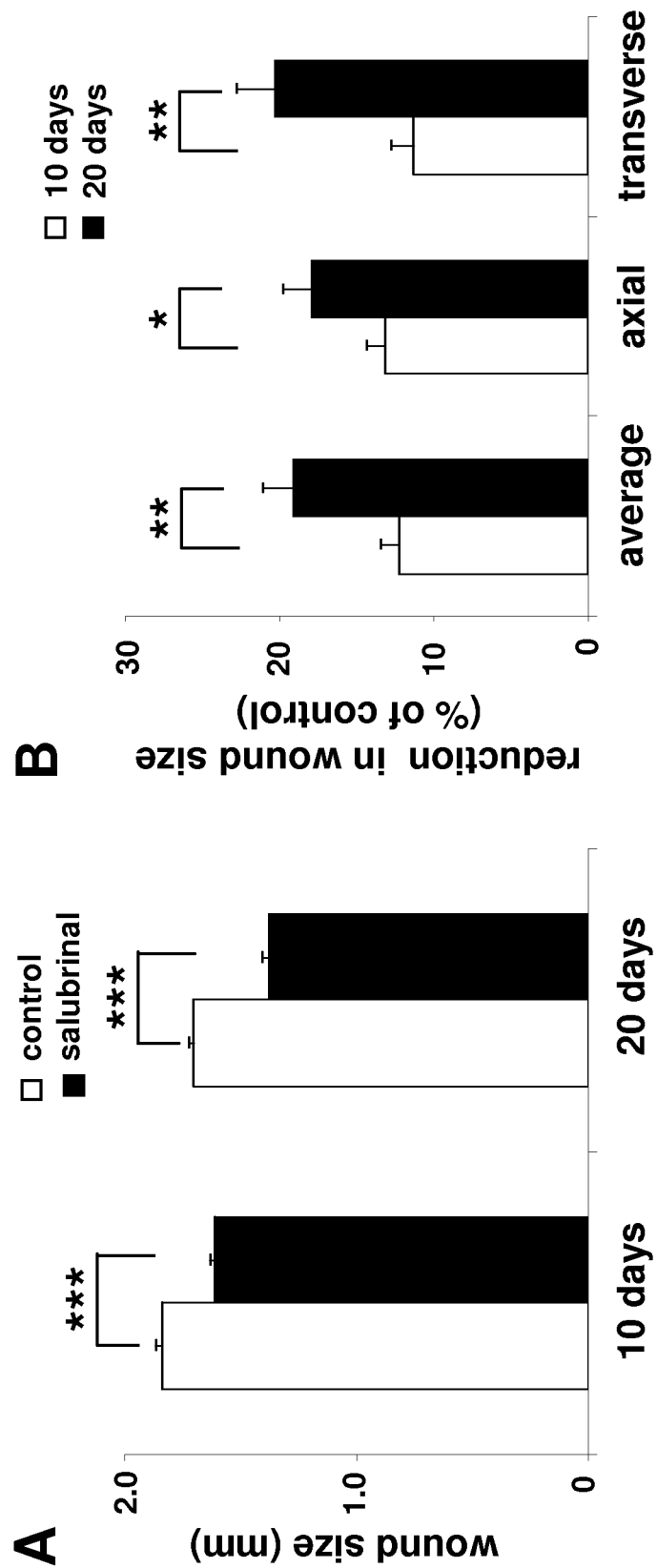
FIG. 17. Reduced wound size in salubrinal-injected tibiae. Note that "average" represents the mean value of "axial" and "transverse" sizes; (*=$p<0.05$; =$p<0.01$, *=$p<0.001$). (A) Wound size on the medial surface (mm). (B) Reduction in wound size (% of control).

Micro CT images revealed that local injection of salubrinal accelerated closure of the surgical hole in both tibia sections 10 and 20 days after surgery in rat tibia (FIG. 17). Ten day after surgery, the size of the wounds on the medial cortex was smaller by 12.3% ($1.841\pm0.021$ mm in control and $1.614\pm0.014$ mm in salubrinal; $p<0.001$). In 20 days, the size was further decreased by 19.1% ($1.699\pm0.019$ mm in control and $1.375\pm0.033$ mm in salubrinal; $p<0.001$). In the normalized changes to the contralateral control, reductions in overall wound size ($p<0.01$) together with its axial size ($p<0.05$) and a transverse size ($p<0.01$) on day 20 were more significant than those on day 10. Without being bound by theory, it is believed herein that these results suggest that the effects of salubrinal last longer than the initial 10 day treatment period.

Figure 18:
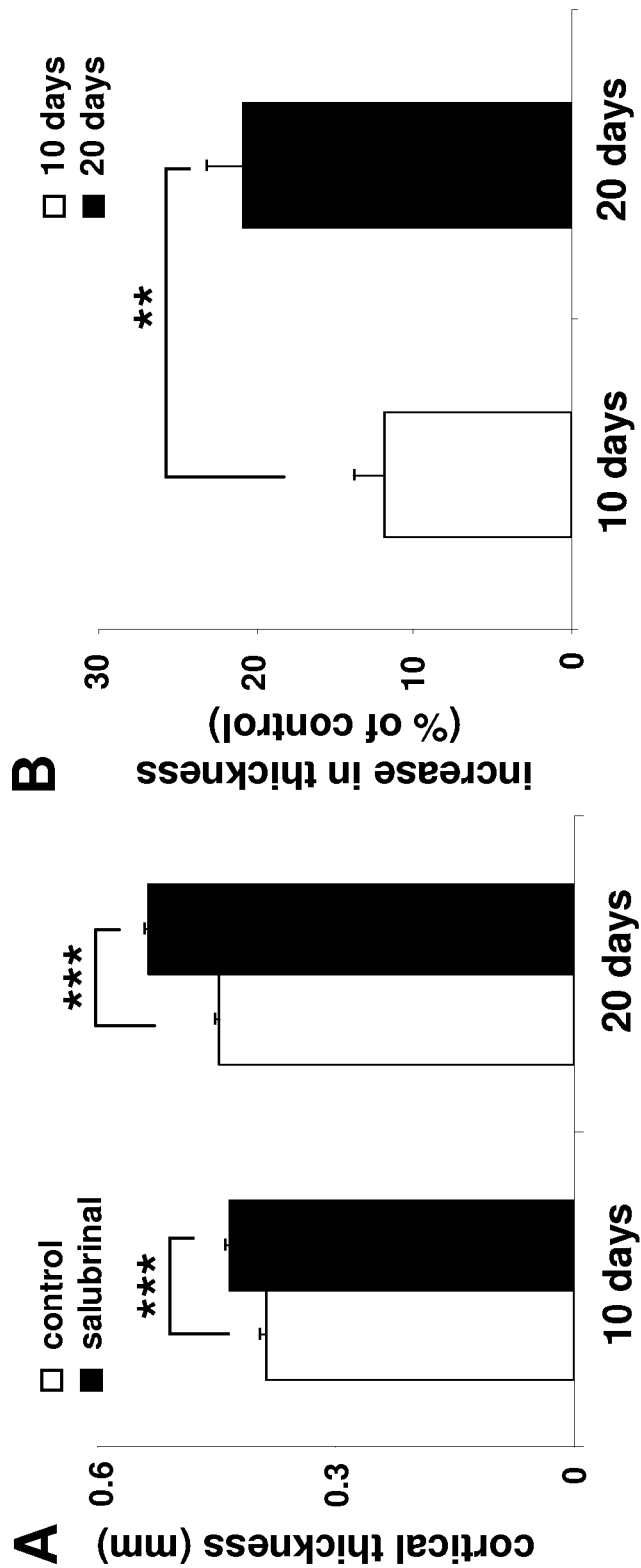
FIG. 18. Increased cortical thickness in salubrinal-injected tibiae. (A) Comparison between the control and salubrinal groups. (B) Normalized Increase normalized by the control thickness. Note that % of the increase was larger at 20 days than 10 days (=$p<0.01$; and *=$p<0.001$).

In accordance with the wound size, micro CT images also displayed an increase in cross-sectional cortical thickness by local administration of salubrinal (FIG. 18). Salubrinal elevated cortical thickness by 11.6% ($0.389\pm0.007$ mm in control and $0.434\pm0.006$ mm in salubrinal; $p<0.001$) on day 10, and by 20.3% ($0.446\pm0.008$ mm in control and $0.537\pm0.005$ mm in salubrinal; $p<0.001$) on day 20. The normalized change in cortical thickness on day 20 was more significant than that on day 10 ($p<0.01$).

Example 14

Figure 20:
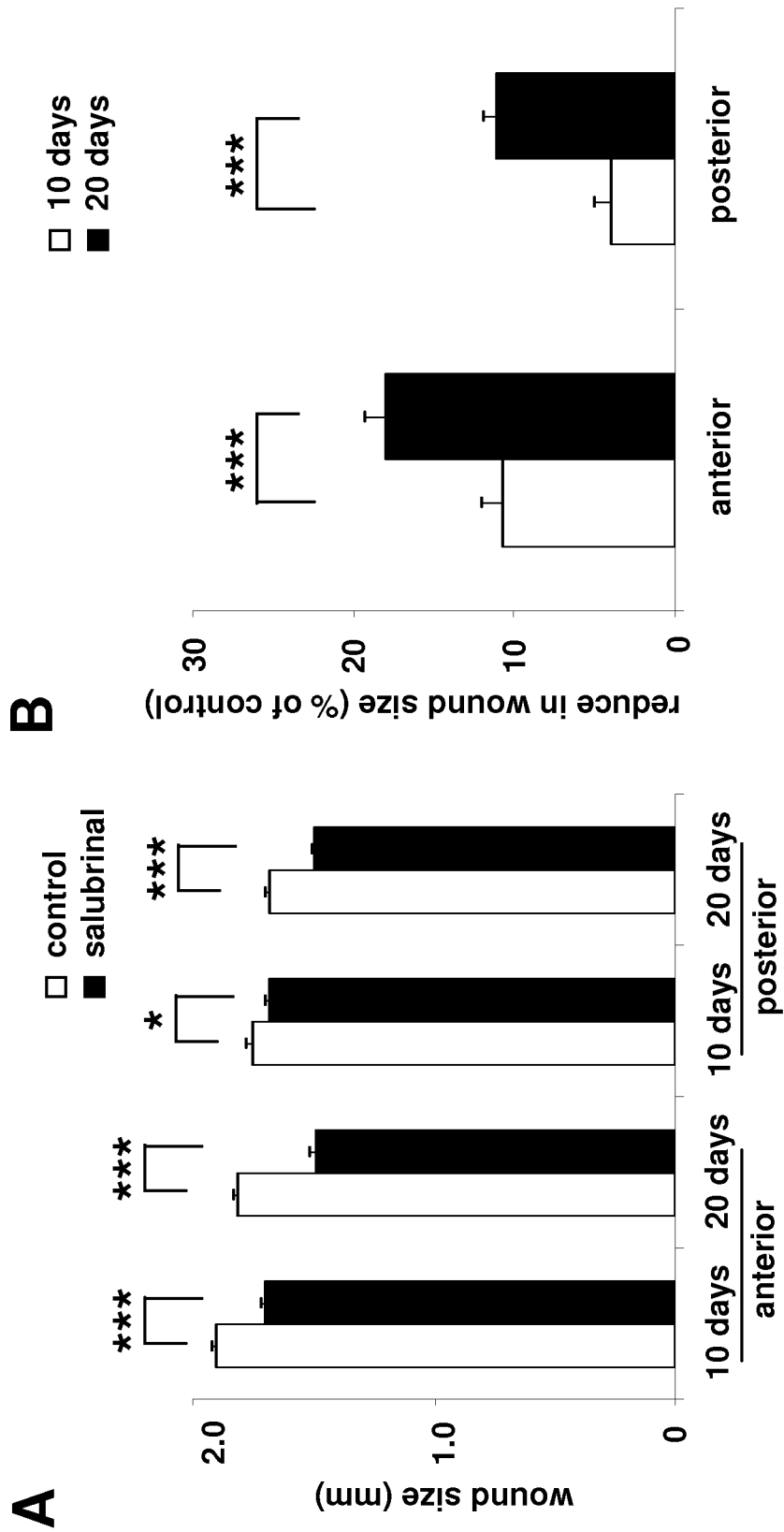
FIG. 20. Reduced wound size in salubrinal-injected femurs; (*=$p<0.05$; and ***=$p<0.001$). (A) The wound sizes on the anterior and posterior surfaces are shown (in mm). (B) Reduction in the wound size (% of control) in both the anterior and posterior surfaces.

Rat femur—healing of surgical wounds. A surgical hole with ~2.0 mm in diameter was generated in the left and right femurs of twenty female SD rats (~8 weeks, body weight ~180 g). The holes were drilled through the femur from the anterior surface to the opposite cortex (posterior surface) in the middle of the femur. During the first 5 days, 100 μl of salubrinal solution at dosage of 0.025 mg/kg was injected subcutaneously to the left limb and a PBS solution (vehicle control) in the right limb. The injection site was closed to the anterior surgical hole. Rats were sacrificed on days 10 or 20 after surgery, and the axial and transverse hole sizes as well as cortical thickness (1.5 mm proximal and distal to the center of the hole) were determined with micro CT. Micro CT images showed that local injection of salubrinal accelerated the closure of the surgical hole in both 10 and 20 days after surgery (FIG. 19). Regarding the anterior holes, the size of the wounds 10 days after surgery was smaller in the salubrinal treated group by 10.8% ($1.905\pm0.018$ mm in control and $1.700\pm0.021$ mm in salubrinal; $p<0.001$). The size in 20 day samples was further decreased by 18.0% ($1.812\pm0.017$ mm in control and $1.486\pm0.026$ mm in salubrinal; $p<0.001$). The posterior holes also exhibited reduction in size by 4.1% (postoperative 10 days; $p<0.05$) and 11.1% (postoperative 20 days; $p<0.001$) by administration of salubrinal (FIG. 20A). Note that the reduction in the wound size on day 20 was more significant than those on day 10 in both the anterior and posterior holes (both $p<0.001$) (FIG. 20B).

Figure 21:
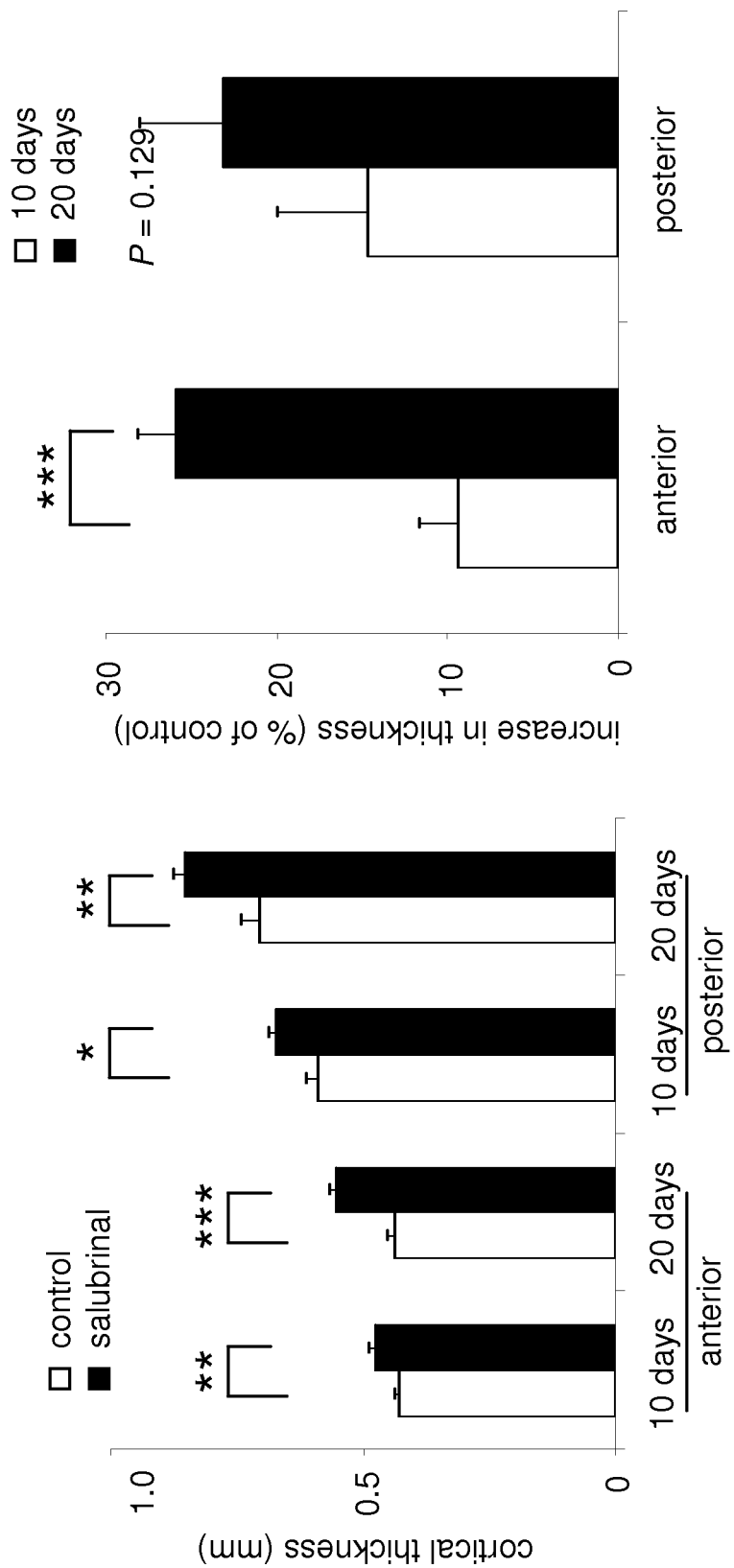
FIG. 21. Increased cortical thickness in the salubrinal-injected femurs (*=$p<0.05$; =$p<0.01$; and *=$p<0.001$): (A) Comparison between the control and salubrinal groups for the anterior and posterior surfaces. (B) Normalized increase in the control thickness.

Micro CT images also demonstrated an increase in the cross-sectional cortical thickness by local administration of salubrinal (FIG. 21). In the anterior hole, for example, administration of salubrinal increased cortical thickness by 11.0% ($0.429\pm0.007$ mm in control and $0.476\pm0.012$ mm in salubrinal; $p<0.01$) on day 10, and 25.7% ($0.439\pm0.011$ mm in control and $0.551\pm0.014$ mm in salubrinal; $p<0.001$) on day 20. Furthermore, the posterior hole exhibited the similar increase: 13.8% (postoperative 10 days; $p<0.05$) and 21.3% (postoperative 20 days; $p<0.01$) (FIG. 21).

Example 15

Pig Osteonecrosis Model. Analysis of blood circulation in a pig osteonecrosis model in the femoral head. Osteonecrosis of the femoral head is necrotic bone degradation in the hip joint, in which interruption of blood supply towards the proximal femur is considered one of its major causes. This model is used to assess test materials for the ability to stimulate healing of the femoral head and/or develop a joint-preserving treatment (Kim H K, et al., J Bone Joint Surg Am 83:688-697

(2001)). The model allows evaluation of blood supply to the femoral head. Following surgery to prepare the model, as much as 90% of blood circulation to the femoral head may be blocked. CT and optical imaging are employed to trace microfil casted blood vessels in both control, positive control, and test material treated samples.

Materials and Methods. Surgery Procedures. Female Yorkshire piglets (6-8 kg weight) are used. Following pre-medication, general anesthesia is induced with 2% isoflurane. A longitudinal incision is made over the hip. Gluteus and hip abductor muscles overlying the hip joint are identified and separated using retractors. The hip joint capsule is partially incised to expose the lateral aspect of the femoral head and neck. Ligamentum teres are visualized by subluxing the femoral head and transecting with a curved scissor. Two sutures are then passed around the femoral neck and tied tightly to disrupt the blood vessels leading to the femoral head.

Preparation of microfil casts: After 3 hr, a midline incision is made to expose the abdominal aorta and the inferior vena cava. A needle (#18) is inserted distally, and the cannula is used for perfusion. The pig is injected with 60 ml of heparinized saline (0.9% sodium chloride with 10,000 unit heparin) via abdominal aorta, and infused with a radiopaque, lead-containing, liquid, low-viscosity polymer (Microfil MV-122, Flow Tech; Carver, MA). The infusion volume is about 60 ml, and the perfusion pressure is about 100 mmHg (Bolland B J, et al., Bone 43:195-202 (2008)).

CT imaging analysis of blood circulation: In order to evaluate blood circulation in the necrotic and control proximal femora, CT imaging is performed on microfil casted animals. The three-dimensional geometrical data of vascular systems and their association with femoral structures are imaged with a resolution of about 400 µm in transverse plane and about 700 µm in cranial caudal direction.

Angiogram of a pig lower body is performed to verify that blood flow to the ligated leg is successful, such as via the iliac, common and superficial femoral, deep femoral, and circumflex arteries.

Estimation of blood circulation in the femoral head: Focusing on the femoral head, the microfil casted blood vessels are evaluated. In the control section, a network of yellow-stained vessels is visible. In the femoral head treated for induction of osteonecrosis, however, staining was significantly reduced.

Forty-eight hrs after surgery, the femoral head is harvested and decalcified. CT imaging is conducted through the section consisting of the metaphysis and the epiphysis (FIG. 22). A clear difference in blood circulation in the epiphysis between two sections is observed.

In this pig model, CT and optical imaging are employed to evaluate blood circulation in the control and infarcted femoral head sections. The results support validity of this pig model for studying avascular osteonecrosis of the femoral head.

Example 16

Rodent ovariectomy. Test animals are available from The Jackson Laboratory (Bar Harbor, Me.). Briefly, place the rodent in ventral recumbency. The surgical area in this procedure is the dorsal surface, from the last rib midway to the pelvis. With the scalpel, make a small skin incision on midline below the last rib. Bluntly dissect the skin from the muscle to either side of the incision. Through the skin incision, incise the muscle wall about 1 cm to the left side, 0.5-1 cm below the last rib to enter the abdominal cavity. With forceps, gently grasp and exteriorize the periovarian fat pad located immediately inside the body wall. Identify the ovary, which is a small red round tissue—do not handle the ovary. Disruption of the ovary may result in abdominal implantation of ovarian tissue. While holding the periovarian fat pad with forceps in one hand, use mosquito hemostats in the other hand to clamp and crush the fallopian tube located between the ovary and the body of the uterus. Release the hemostats, and cut the crushed area and some periovarian fat (but do not cut the ovary) with scissors to excise the ovary. Place the ovary in a sterile gauze pad and place it away from the surgical area. Replace the uterus body back into the abdominal cavity. One interrupted throw of absorbable suture may be placed in the muscle layer to close the body wall incision. Repeat steps on the right side. Close the skin incision with one or two sterile surgical wound clips.

The test on the ovariectomized rodent is carried out as follows. Salubrinal is locally administered through injection to a bone marrow cavity in the proximal tibia. A total volume of 20 µl PBS is injected to the left hindlimb with or without 0.025 mg/kg (100 µM) salubrinal (Calbiochem) using a micro-syringe with a 0.5-inch #26-gauge needle.

Example 17

Determination of Anabolic Activities of Test Compounds with Ovariectomized (OVX) Rat. Additional details are described in Rixon, et al (1994), J. Bone, 9: 1179-1189. Briefly, Sprague-Dawley rats weighing 255-275 g are purchased from Charles River (St. Constant, QC, Canada). For each experiment, 105 rats are weighed and divided into 21 groups, each with 5 rats, with comparable mean body weights between 260 and 265 g. These 21 groups are divided into 6 experimental groups consisting of 1 group of 5 animals for 0-time controls and 5 groups of 20 rats each which provided one group for normal or sham-ovariectomized (Sham-OVX) controls, one for OVX controls, and 3 for OVX rats treated with various test compounds. Sham OVX and OVX are performed under anesthesia by the standard dorsal approach. For sham-OVX, the ovaries are exteriorized, but not removed. Except for the normal, unoperated rats, day 0 for each experimental group is the day of OVX. Starting 2 weeks later, designated groups of rats are given daily subcutaneously injections of compounds and/or compositions described herein (1 nmole/100 g of body weight) dissolved in acidic saline (0.15M NaCl containing 0.001N HCl). The OVX control animals receive comparable volumes of diluent solution only. The preparation and analysis of cortical and trabecular bone is carried out as described in M. Gunness-Hey & J. M. Hock, Metab. Bone Dis. Rel. Res., 5:177-181 (1984). Femurs are isolated, cleaned, and their lengths from the proximal, collum femoris to the distal condylar surfaces are measured. Each bone is then cut in half at mid-diaphysis and the proximal half discarded. After removing the epiphysis, each half-femur is split lengthwise and the marrow washed out with distilled water. Each half is placed under a dissecting microscope and the trabecular (cancellous) bone is scraped out. The isolated trabecular bone and the remaining cortical (compact bone) are dried at 55° C. for at least 24 hr., and weighed to determined dry mass, expressed as mg/distal half-femur. After at least 3 days, the trichloroacetic acid extract is quantitatively removed and saved. The calcium contents of the pooled trichloroacetic acid extracts from each cortical and trabecular bone sample are measured using the cresolphthalein complex one colorimetric procedure, using a kit, such as that available from CIBA-Corning Diagnostics.

What is claimed is:

1. A method for treating a disease resulting from integrated stress response-induced apoptosis in a population of cells, the method comprising the step of administering to a patient in need of relief a therapeutically effective amount of an inhibitor of eIF2α dephosphorylation, where the therapeutically effective amount is capable of decreasing the apoptosis;
   wherein the apoptosis is endoplasmic reticulum stress-induced apoptosis; and,
   wherein the disease is a bone disease, injury, or defect, or a combination thereof.

2. The method of claim 1 wherein the apoptosis is endoplasmic reticulum stress-induced apoptosis resulting in upregulation of one or more phosphorylases in the population of cells.

3. The method of claim 1 wherein the cell population comprises an osteoblast.

\* \* \* \* \*

UNITED STATES PATENT AND TRADEMARK OFFICE
CERTIFICATE OF CORRECTION

| | | |
|---|---|---|
| PATENT NO. | : 9,056,105 B2 | Page 1 of 1 |
| APPLICATION NO. | : 13/055399 | |
| DATED | : June 16, 2015 | |
| INVENTOR(S) | : Hiroki Yokota et al. | |

It is certified that error appears in the above-identified patent and that said Letters Patent is hereby corrected as shown below:

In the Claims

Column 27, Line 2, cancel the text beginning with "1. A method for treating a disease" to and ending with "combination thereof." in column 27, Line 11, and insert the following claim:

--1. A method for treating a disease resulting from integrated stress response-induced apoptosis in a population of cells, the method comprising the step of administering to a patient in need of relief a therapeutically effective amount of an inhibitor of elF2α dephosphorylation, wherein the inhibitor is salubrinal or a pharmaceutically acceptable salt thereof, where the therapeutically effective amount is capable of decreasing the apoptosis;
  wherein the apoptosis is endoplasmic reticulum stress-induced apoptosis; and,
  wherein the disease is selected from a group consisting of a bone fracture, osteonecrosis, pediatric hip necrosis, osteoporosis and osteopenia.--

Signed and Sealed this
Twelfth Day of January, 2016

Michelle K. Lee
*Director of the United States Patent and Trademark Office*